United States Patent
Gerber et al.

(10) Patent No.: US 9,764,076 B2
(45) Date of Patent: Sep. 19, 2017

(54) AUTHENTICATION SYSTEM UTILIZED IN A SORBENT-BASED DIALYSIS SYSTEM FOR THERAPY OPTIMIZATION

(71) Applicant: Medtronic, Inc., Minneapolis, MN (US)

(72) Inventors: Martin T. Gerber, Maple Grove, MN (US); Daniel Bloomberg, Minneapolis, MN (US); David B Lura, Maple Grove, MN (US); VenKatesh R. Manda, Stillwater, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/838,112

(22) Filed: Aug. 27, 2015

(65) Prior Publication Data

US 2015/0359954 A1    Dec. 17, 2015

Related U.S. Application Data

(63) Continuation-in-part of application No. 14/261,751, filed on Apr. 25, 2014.

(Continued)

(51) Int. Cl.
  *B01D 35/00*    (2006.01)
  *A61M 1/36*    (2006.01)
  *G06K 19/077*    (2006.01)

(52) U.S. Cl.
  CPC ............ *A61M 1/36* (2013.01); *A61M 1/3681* (2013.01); *G06K 19/077* (2013.01);
  (Continued)

(58) Field of Classification Search
  None
  See application file for complete search history.

(56) References Cited

U.S. PATENT DOCUMENTS 6,468,424 B1  10/2002  Donig
6,685,831 B2   2/2004  Donig
(Continued)

FOREIGN PATENT DOCUMENTS

CN  103037917   4/2013
EP    0341799  11/1989
(Continued)

OTHER PUBLICATIONS

International Search Report from PCT/US2015/015205 mailed Apr. 23, 2015.

(Continued)

*Primary Examiner* — Richard Gurtowski
(74) *Attorney, Agent, or Firm* — Kenneth Collier; Roger Hahn

(57) ABSTRACT

A dialysis authentication and management system comprising at least one dialysis component having at least one authentication component affixed thereon. The dialysis component can be any one of a dialyzer, sorbent cartridge, recharger or any other dialysis component. The authentication component can be selected from the group of a radio-frequency identification marker, a bar code, a one-wire security component, and a wireless authentication component. The authentication system can ensure that all components used are in proper usable condition and/or certified. The system can also manage the recharging of rechargeable components, and optionally manage dialysis therapy.

20 Claims, 22 Drawing Sheets

Related U.S. Application Data

(60) Provisional application No. 61/945,095, filed on Feb. 26, 2014.

(52) U.S. Cl.
CPC ............... *A61M 2205/3375* (2013.01); *A61M 2205/6009* (2013.01); *A61M 2205/75* (2013.01)

(56) References Cited

U.S. PATENT DOCUMENTS

| | | |
|---|---|---|
| 7,755,488 B2 | 7/2010 | Dvorsky |
| 7,955,295 B2 | 6/2011 | Lee |
| 8,496,609 B2 | 7/2013 | Childers |
| 2001/0040127 A1 | 11/2001 | Donig |
| 2002/0188259 A1 | 12/2002 | Hickle |
| 2009/0009290 A1 | 1/2009 | Kneip |
| 2009/0012448 A1 | 1/2009 | Childers |
| 2009/0012449 A1 | 1/2009 | Lee |
| 2009/0069925 A1 | 3/2009 | Dattolo |
| 2009/0076434 A1 | 3/2009 | Mischelevich |
| 2009/0079578 A1 | 3/2009 | Dvorsky |
| 2009/0275883 A1 | 11/2009 | Chapman |
| 2009/0289796 A1 | 11/2009 | Blumberg |
| 2009/0295659 A1 | 12/2009 | Blumberg |
| 2011/0017665 A1 | 1/2011 | Updyke |
| 2011/0048101 A1 | 3/2011 | Heide |
| 2011/0205134 A1 | 8/2011 | Blumberg |
| 2011/0209212 A1 | 8/2011 | Newlin |
| 2013/0062265 A1 | 3/2013 | Balschat |
| 2013/0175373 A1 | 7/2013 | Morgan |
| 2014/0027380 A1 | 1/2014 | Childers |
| 2015/0238673 A1 | 8/2015 | Gerber |
| 2015/0359954 A1 | 12/2015 | Gerber |

FOREIGN PATENT DOCUMENTS

| | | |
|---|---|---|
| EP | 2247926 B1 | 4/2012 |
| EP | 1449548 B1 | 1/2014 |
| EP | 2258419 B1 | 1/2014 |
| WO | 2012120078 A2 | 9/2012 |
| WO | 2014121909 | 8/2014 |

OTHER PUBLICATIONS

Written Opinion in App. No. PCT/US2016/048814 dated Jan. 17, 2017.

Office Action in Chinese Application No. 201510086368.9, Dated Oct. 16, 2016.

Office Action in U.S. Appl. No. 14/261,751, Dated Sep. 19, 2016.

AUTHENTICATION SYSTEM UTILIZED IN A SORBENT-BASED DIALYSIS SYSTEM FOR THERAPY OPTIMIZATION

CROSS REFERENCE

This application is a continuation-in-part (CIP) of U.S. application Ser. No. 14/261,751, filed Apr. 25, 2014, which claims priority to U.S. Provisional Application No. 61/945,095, filed Feb. 26, 2014, each of which is incorporated herein by reference in its entirety.

FIELD OF THE INVENTION

The present invention relates to an authentication and tracking system that can be used for therapy optimization of a sorbent-based dialysis system. The present invention can authenticate dialysis components to eliminate counterfeits and manage product features such as number of recharges for reusable sorbent modules and proper filling for caddies, among others. The present invention can be used to manage correct pairing of a dialysis component with a specific patient, thereby improving efficiency of the dialysis system and mitigating the risk of transferring infectious disease. The dialysis system can be optimized based on the data transferred from the authentication system, including the patient's information. The present invention can provide a remote access to the patient information, which improves the overall patient management and flexibility of the dialysis therapy.

BACKGROUND

Therapeutic outcome of hemodialysis treatment may be affected by many factors, such as conditions of an individual patient, treatment options, proper settings of the dialysis system, usage of consumables for the dialysis, events occurred during the therapy, and relevant environmental factors. Individual components of a dialysis system including the sorbent cartridge must work together properly to provide sufficient structural and functional basis for the optimized therapy.

In a sorbent dialysis system, the spent dialysate is re-circulated through a sorbent cartridge rather than being discarded. The sorbent cartridge contains layers of sorbent materials, which selectively remove specific toxins, or break down toxins, in the dialysate. One of the drawbacks of sorbent dialysis systems is the high cost due to expensive materials used in the sorbent cartridges. Disposing of the cartridges after each use generates waste and also drives up the costs. Regeneration of some or all of the components of a sorbent cartridge for reuse of will lower long-term costs.

In general, only manufacture-designed or certified products are to be used in the dialysis system. Improper usage of dialysis components may cause decreased performance of the system, which endangers patient's safety. Improper usage may include using non-certified products, using rechargeable components that are not fully recharged or beyond their useful life, using dialysis components that do not match the need of particular patients. Additionally, since many dialysis components are in contact with the patient through blood or other fluid communications, cross-usage of dialysis components between patients are strictly prohibited in order to avoid contamination.

Hence, there is a need for methods and systems identifying the specific components of a dialysis system, such as a modular sorbent cartridge with detachable components or parts. There is a need for tracking dialysis components to ensure that certified components are used within their useful lives by the correct patients. There is a need for a system by which individual reusable modules of a modular sorbent cartridge can be tracked to ensure correct sorbent materials are used within their useful lives by the correct patients. There is a further need for methods and systems by which patient information can be identified, updated, easily accessed. The patient information such as prior session data can be used to set up the dialysis system for therapy optimization directed to the particular patient.

SUMMARY OF THE INVENTION

The first aspect of the invention is directed to a dialysis authentication system, which comprises at least one authentication component for managing a sorbent-based dialysis system containing data corresponding to at least one dialysis component in the dialysis system; at least one identifier to read the data of the at least one authentication component; and a processor to receive the data from the at least one identifier, wherein the data are processed by the processor for making determination regarding the at least one dialysis component.

In any embodiment of the first aspect of the invention, the authentication component can be affixed on any one or more selected from the group of a dialyzer, sorbent cartridge, and recharger.

In any embodiment of the first aspect of the invention, the dialysis authentication can be selected from a group comprising a radio-frequency identification (RFID) marker, a bar code, a one-wire security component, and a wireless authentication component.

In any embodiment of the first aspect of the invention, the authentication component can contain an embedded memory.

In any embodiment of the first aspect of the invention, the authentication component can contain a RFID chip and a Memory chip bonded in a smart card.

In any embodiment of the first aspect of the invention, the authentication component can be readable and writable that allows the data of the authentication component to be updated.

In any embodiment of the first aspect of the invention, the processor can determine non-certified components or counterfeit components based on the data received from the authorization component.

In any embodiment of the first aspect of the invention, the authentication system can further comprise a patient authentication component that stores patient information including at least one of patient prescription, treatment history, and cartridge size information.

In any embodiment of the first aspect of the invention, the patient authentication component can be one of an implantable device, a card-like device, and a wrist-band device.

In any embodiment of the first aspect of the invention, the identifier can communicate with the authentication component and the patient authentication component, and the data from the authentication component and the patient authentication component can be communicated to the processor for determining the optimized setting of the dialysis system for the patient regarding the dialysis component.

In any embodiment of the first aspect of the invention, the processor can determine one or more of whether the dialysis component matches the patient, whether setting of the dialysis component is proper, and any changes of the setting to be made for optimized performance, based on the data received from the first, second, third, or fourth authentication components.

In any embodiment of the first aspect of the invention, the identifier can be affixed onto a second dialysis component to read the authentication component, and the processor can determine whether the dialysis component having the authentication component matches the second dialysis component.

In any embodiment of the first aspect of the invention, the identifier can be a multimode type reader that is able to communicate with at least two different types of the authentication component.

In any embodiment of the first aspect of the invention, when the at least one authentication component includes two or more authentication components, the identifier can distinguish the two or more authentication components from each other.

Any of the features disclosed as being part of the first aspect of the invention can be included in the first aspect of the invention, either alone or in combination.

The second aspect of the invention relates to a method of managing a dialysis system for performing dialysis, via radio signals, comprising reading a first data from a first authentication component corresponding to a first dialysis component by an identifier, reading a second data from a second authentication component corresponding to a second dialysis component or a patient by the identifier, receiving the first data and the second data by a processor from the identifier, making determination by a processor based on the first data and the second data regarding the first dialysis component in view of the second dialysis component or the patient; and controlling setting of the first dialysis component for optimized performance in view of the second dialysis component or the patient.

In any embodiment of the second aspect of the invention, the method can further comprise storing data in at least one of the first authentication component and the second authentication component regarding the dialysis, during or after the dialysis ends.

Any of the features disclosed as being part of the second aspect of the invention can be included in the second aspect of the invention, either alone or in combination.

A third aspect of the invention is related to a method comprising the steps of: reading data from an authentication component affixed on a rechargeable component used in sorbent-based dialysis by an identifier, communicating the data derived from the authentication component to a processor by the identifier, determining whether to start a recharge of the rechargeable component by the recharger based on the data received by the processor; and controlling a recharger used to recharge the rechargeable component to selectively recharge based on the determination made by the processor.

In any embodiment of the third aspect of the invention, the step of determining can comprise determining one or more of whether the rechargeable component is stored too long according to a predetermined standard, whether the rechargeable component is not fully recharged, and whether the rechargeable component reaches a limit of recharging.

In any embodiment of the third aspect of the invention, the authentication component can be an RFID component.

Any of the features disclosed as being part of the third aspect of the invention can be included in the third aspect of the invention, either alone or in combination.

A fourth aspect of the invention is related to a method comprising: reading data of an authentication component affixed on a multi-use cartridge by an identifier affixed on a hemodialysis system; communicating the data of the authentication component to a processor by the identifier; determining by the processor whether the cartridge is to be properly used according to the data communicated to the processor; and controlling a hemodialysis therapy according to the determination made by the processor.

In any embodiment of the fourth aspect of the invention, the step of determining can comprise determining one or more of whether the cartridge is stored too long according to a predetermined standard, whether the cartridge is not fully recharged, whether the cartridge reaches a limit of recharging, and whether the cartridge matches a patient.

In any embodiment of the fourth aspect of the invention, the authentication component can be an RFID component.

Any of the features disclosed as being part of the fourth aspect of the invention can be included in the fourth aspect of the invention, either alone or in combination.

DETAILED DESCRIPTION OF THE INVENTION

Figure 1A:
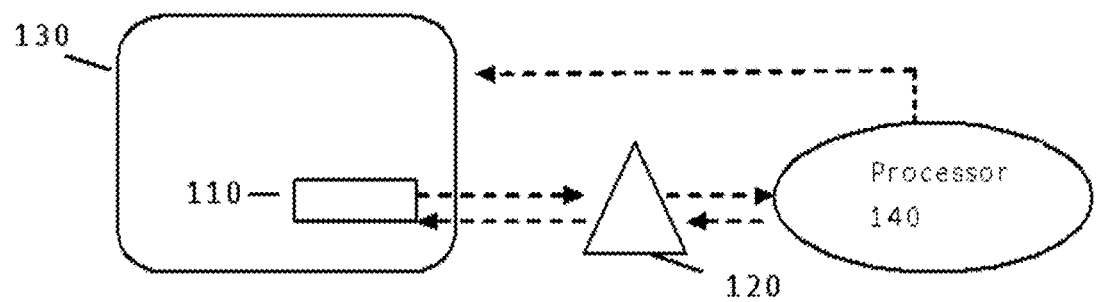
FIGS. 1a-1c show different examples of an authentication system having at least one authentication component, an identifier, and a processor, where signals are being transferred within the system.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "affixed" means permanently or temporarily attached.

An "antenna" is a component capable of sending or receiving electromagnetic waves.

The terms "authentication component" or "identification component" may be used interchangeably, and refer to a component that allows for identification of a particular component to which the authentication component is attached.

A "bar code" is a computer readable pattern of parallel lines and spaces of variable thickness that identifies the component to which the barcode is attached.

The term "bonded" refers to a component being either embedded in, or affixed to, another component.

A "card-like" device is a device that has a thin, substantially planar shape.

The term "cartridge" refers to any container designed to contain a powder, liquid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

"Cartridge size information" refers to information concerning the amount of one or more sorbent materials within a sorbent cartridge.

The term "caddy" refers to a container detachably removable from a dialysis system, the caddy configured to hold one or more other containers. In any embodiment the caddy can include one or more connectors for fluid connection from the containers to the dialysis system.

The term "cation infusate container" or "infusate container" refers to a source from which cations can be obtained. Examples of cations include, but are not limited to, calcium, magnesium and potassium. The source can be a solution containing cations or a dry composition hydrated by the system. The cation infusate container is not limited to cations and may optionally include other substances to be infused into a dialysate or replacement fluid; non-limiting examples can include glucose, dextrose, acetic acid and citric acid.

A "certified product," "certified component" or "certified part" is a component of a dialysis system wherein components, parts, modules, sections of the dialysis system have been determined to be certified. In some cases, certification can indicate that the component is capable of being safely and effectively used in the system. A component that is not a certified component can be said to be "non-certified" or "counterfeit."

The term "communicate" refers to the sending or receiving of signals from one component to another component.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present.

The term "console" refers to an apparatus or a part of the apparatus that has a control function. In some instances, a console can control the apparatus based on data received or stored in the console.

The term "containing data" refers to a component from which particular information can be obtained, including but not limited to, patient information, system information and component information.

A "controller," "control unit," "processor," or "microprocessor" is a device which monitors and affects the operational conditions of a given system. The operational conditions are typically referred to as output variables of the system wherein the output variables can be affected by adjusting certain input variables.

The term "controlling" refers to the managing of parameters within a system.

The term "detachable" or "detached" relates to any component of the present invention that can be separated from a system, module, cartridge or any component of the invention. "Detachable" can also refer to a component that can be taken out of a larger system. In certain instances, the components can be detached with minimal time or effort, but in other instances can require additional effort. The detached component can be optionally reattached to the system, module, cartridge or other component. A detachable module can often be part of a reusable module.

A "detector" is a device for receiving digital information sent from the antenna on the authentication component.

The term "determination" refers to the process of causing or setting a particular control or setting for a process or method.

"Dialysate" is the fluid that passes through the dialyzer and does not pass through the membrane into the blood flow.

"Dialysis" or "hemodialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis authentication system" is a system for use in dialysis comprising at least one authentication component affixed to at least one dialysis component.

A "dialysis component" is any component that is designed to be used for dialysis or as a part of a dialysis system used for any one or more of hemofiltration, hemodiafiltration, ultrafiltration, and/or peritoneal dialysis.

A "dialysis system" is a system for performing dialysis, including some or all dialysis components necessary for dialysis.

The term "dialyzer" refers to a cartridge or container with two flow paths separated by semi-permeable membranes.

One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

An "embedded memory" is a circuit or circuits within a component that can store data.

The term "identifying information" refers to information about a component or class of components. Identifying information can refer to information that identifies the particular component in question, information that identifies the type of component, or information that identifies the manufacturer of the component.

An "implantable" component or tag refers a component or tag that can be implanted into a body part of a patient.

"Infusate" is a solution of one or more salts for the adjustment of the composition of a dialysate.

A "limit of recharging" refers to the number of times a rechargeable component can be used and recharged safely.

"Managing" refers to the process of tracking or controlling the use of a system or the process of controlling parameters used by a system.

The term "matches" refers to a state wherein a particular user or setting is proper for use with a particular component.

"Memory" is a device capable of storing digital information on a temporary or permanent basis.

A "memory chip" is a component that is capable of storing information and that can be embedded into another component.

A "memory device" is a device for recording digital information that can be accessed by a microprocessor, such as RAM, Dynamic RAM, microprocessor cache, or Flash memory.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "multi-use" refers to a component that can be safely used more than one time, possibly with recharging, as defined herein, of the component between uses.

The term "non-reusable" or "single-use" refers to a component that cannot be reused in the component's current state. In certain instances, the term non-reusable can include the concept of being disposable, but is not necessarily limited to just being disposable.

A "one-wire security component" is a component comprising two parts that can be connected by a wire, wherein the first part sends an identification signal to the second part, and then the second part sends a unique identification signal back to the first part, with both transmissions occurring over the same wire. Although the term wire is used, any type of contact between one or more surfaces sufficient to provide for transmission of an electrical signal between the two surfaces is also encompassed by the invention. For example, two plates in electrical contact can be considered to be connected by a wire.

The terms "optimized setting," "optimized performance," "optimized therapy outcome" refer to controlling the proper use of one or more components of an apparatus, and in some instances, may include adjusting the settings of the one or more components, in order to achieve the best possible outcome of the functionality of the apparatus. In some instances, the optimized setting is directed towards a particular subject, such as a patient, to protect the patient's best interest. For example, the optimized setting of a dialysis system can include, but not limited to, using certified products, maintaining safe use of a rechargeable component, ensuring the dialysis component matches the dialysis system, and the settings of the dialysis system match the particular patient.

The terms "pathway," "conveyance pathway," "fluid flow path," and "flow path" refer to the route through which a fluid or gas, such as dialysate or blood travels, or the route an inert gas travels.

"Patient information storage device" or "patient authentication component" refers to authentication component that stores information regarding a patient, including but not limited to, patient identification, medical prescriptions, information of prior sessions, cartridge size, and special events occurred during prior medical treatment, in particular, the dialysis treatment. The patient information storage device may be any type of authentication components.

"Patient information" refers to any data concerning a particular patient, including patient name, medical prescriptions, information of prior sessions, cartridge size, and special events occurred during prior medical treatment, in particular, the dialysis treatment.

A "predetermined standard" is a parameter for use with a device wherein if the device is outside of the predetermined standard, the device is determined to be unsafe to use.

"Prescription" or "patient prescription" refers to one or more system settings for a dialysis session of a patient.

A "processor" is a device which monitors and affects the operational conditions of a given system. The operational conditions are typically referred to as output variables of the system, which can be affected by adjusting certain input variables.

"Product history" refers to any one or combination of features related to the product for the use, type of use, time of use, origin, manufacturer, components, user, and any other but not necessarily limited to, time-dependent data of the product.

The term "pump" refers to any device that causes the movement of fluids or gases by the application of suction or pressure.

"Radio Frequency Identification," "RFID," "RFID tag," "RFID marker," or "RFID chip" refers to a device, component, or electrical circuit of any type capable of transmitting, receiving, or both transmitting or receiving passively or actively, radio frequency signals to and from a receiver.

"Radio signals" refers to electromagnetic radiation with a frequency of between about 3 kHz to about 300 GHz.

The term "read data" refers to the process of receiving information from an authentication component.

The term "readable" refers to a memory component that contains information obtainable by another component.

A "reader" or an "identifier" is a component that is capable of receiving information from an RFID tag, one-wire security component or wireless authentication component, or by scanning a bar code. A "multimode" reader is a type of reader that can read at least two different types of the authentication component, such as a RFID tag and a barcode.

The term "receive data" refers to the process of obtaining information from a source.

A "rechargeable component" is a component that can be used and then placed back into condition for re-use.

A "recharger" is a component that is capable of recharging spent sorbent material to or near its original state. A recharger may be part of the dialysis system, or may be separate from the rest of the system. If the recharger is separate from the rest of the dialysis system, the term may include a separate facility where the spent sorbent material is sent to be returned to, or near, its original state.

"Recharging" refers to the process of treating spent sorbent material or any other dialysis component so as to put the material back in condition for use in sorbent dialysis. Upon a material undergoing "recharging," the material can then said to be "recharged."

"Reusable" refers in one instance to a sorbent material that can be used more than one time, possibly with treatment or recharging of the sorbent material between uses. A reusable or rechargeable component may also refer to a sorbent cartridge that contains a sorbent material that can be recharged by recharging the sorbent material(s) contained within the sorbent cartridge.

A "setting" of a component refers to one or more parameters of a component for use in a dialysis session.

A "smart card" is a component that contains at least one tracking or authentication component.

A "sorbent-based dialysis system" is a dialysis system in which at least a portion of dialysate is passed through a sorbent cartridge containing sorbent materials, in order to remove at least one solute from the dialysate.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent materials" are materials that are capable of removing specific solutes from solution, such as urea.

"Spent dialysate" is a dialysate contacted with blood through a dialysis membrane and contains one or more impurity, or waste species, or waste substance, such as urea.

The term "stored too long" refers to whether a rechargeable or reusable component has been unused or unrecharged for a length of time that makes further use of the component unsafe.

"Storing data" refers to the process of providing data to a memory component wherein the data can be retrieved at a later time.

"Treatment history" refers to relevant information regarding a patient's prior medical treatment, in particular, dialysis treatment, including, but not limited to, prescriptions of the prior treatment, status of dialysis components and settings for a dialysis system for the prior treatment, events occurred during the prior treatment, and medical outcome of the dialysis treatment.

A "unique identifier" is information stored in an authentication component that is capable of distinguishing one component from other components of the same type.

The term "water source" refers to a source from which potable or not potable water can be obtained.

A "wireless authentication component" is an authentication component that transmits identification information to a receiver without being directly connected to the receiver.

A "wrist-band" device refers to a device containing a band-like structure and a functional structure such as an authentication component, the wrist-band device can be attached to a patient's wrist, arm, ankle, or any other parts of the body by the band-like structure.

A "writer" is a component that is capable of transmitting digital information to a reader.

The term "writable" refers to a memory component wherein additional information can be added to the memory.

Dialysis Authentication System

Dialysis authentication systems can be provided for therapy optimization of hemodialysis. A dialysis authentication system can comprise at least one authentication component containing data for use in a dialysis process affixed on a dialysis component, at least one identifier to perform data communication with the authentication component, and a processor to receive the data of the authentication component via the identifier. The processor can further process the data and make determination regarding the dialysis component based on the data received.

Figure 1B:
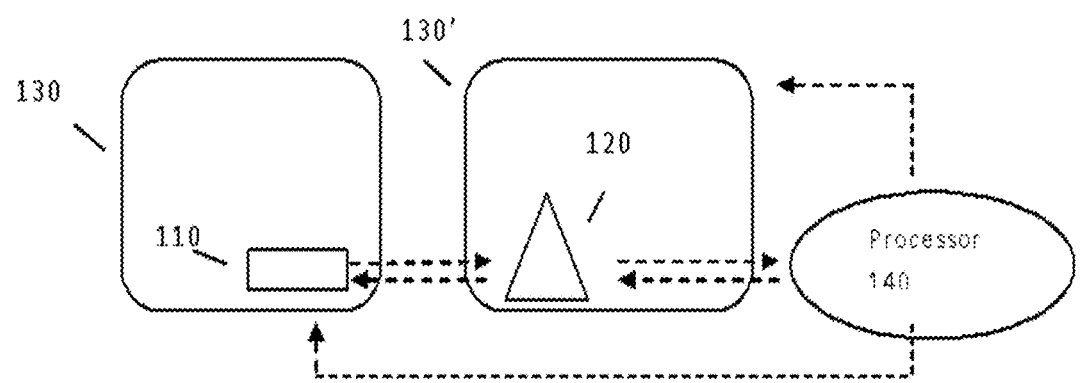
Figure 1C:
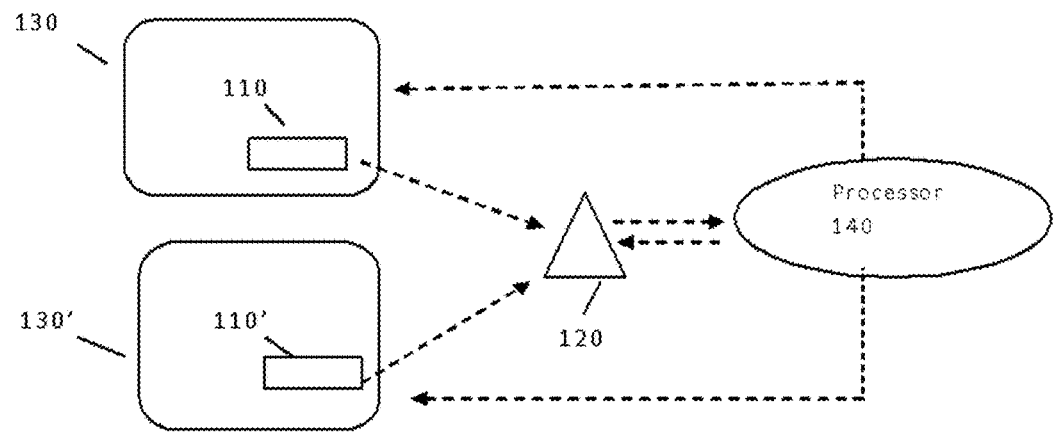

FIGS. 1a-1c show different examples of a dialysis authentication system. FIG. 1a shows the authentication system containing an authentication component 110, which is affixed on a dialysis component 130, to communicate with an identifier 120 through data transferring therebetween. The identifier 120 can emit signals to the authentication component 110, read the authentication component 110, and further transfer the data received from the authentication component 110 to a processor 140.

FIG. 1b shows an authentication system having an identifier 120 affixed upon a dialysis component 130' to communicate with an authentication component 110 of a dialysis component 130. When the two dialysis components are assembled together or brought close to each other, data communication may occur between the identifier 120 and the authentication component 110. Data received by the identifier 120 can further be transferred to the processor 140.

FIG. 1c shows that an identifier 120 can communicate with authentication components 110 and 110' of different dialysis components 130 and 130'. Data received from the authentication components 110 and 110' can then be transferred to a processor 140 via the identifier 120. The processor 140 can then make determination regarding the multiple dialysis components 130 and 130', such as whether dialysis components 130 and 130' are matched with each other. In a non-limiting example, dialysis component 130 may be a recharger and dialysis component 130' may be a cartridge having a reusable module.

In any embodiment of the first, second, third, or fourth aspects of the invention, authentication components 110 can be attached to at least one of a dialyzer, a sorbent cartridge, and a recharger. Authentication components 110 can also be attached to patients and other dialysis components, including but not limited to, caddies, reservoirs, blood tubing, infusates, and other consumables used for the dialysis.

Identifiers 120 can be attached to a dialysis component or be a separate device. An identifier 120 may be a multimode type reader that can communicate with at least two different types of the authentication component. An identifier 120 may distinguish at least two of the authentication components from each other, when the at least two authentication components are available to the identifier at the same time. An identifier 120 may also contain additional information from other sources, such as pre-stored information including those received previously from a different authentication component. The information received or stored in an identifier 120 can be further transferred to a processor 140. An identifier 120 can also receive information from the processor 140.

In any embodiment of the first, second, third, or fourth aspects of the invention, the processor 140 can make a determination based on the received data from the identifier 120 regarding the one or more dialysis components 130. The processor 140 may be a part of the identifier 120, a part of the dialysis component 140 or any other component of the dialysis system, such as a console or a dialysis cabinet. The processor 140 may also be a device that can be connected to the dialysis system through wired or wireless communication. The determination made by the processor 140 can then be displayed on a screen (not shown) to timely notify a user. The screen may be a part of the processor 140, a part of the dialysis component 130, a part of the identifier 120, or a separate device. A user can also be notified the determination result of the processor 140 through sound signals, light signals, or any other suitable means of information delivery.

The processer 140 can correlate dialysis component-specific unique information with user-specific unique information, and correlate manufacture-specific unique identifier with dialysis component-unique information, when such information are received by the processor 140 from the authentication components 110 via the identifier 120. The processor 140 can then determine, for example, whether the dialysis component matches the specific user, and whether the dialysis component is the manufacture-designed or certified product.

The processor 140 may also determine other characteristics of the dialysis components, such as whether the dialysis components are used safely and properly. For example, the processor 140 can determine whether a rechargeable component is fully recharged, whether a sorbent cartridge matches the dialysis system, and whether the settings of the dialysis system are proper for the patient, when the patient information is available from a patient authentication component. The processor 140 can further control the settings of the dialysis system, such as blood flows, ultrafiltration rate, and ultrafiltration profile. The processor 140 may deactivate the use of a dialysis component where an improper use is found.

In non-limiting examples, activation of the authentication system can start from the communication between one or more identifiers 120 and one or more authentication components 110 in response to a particular event. The particular event may occur when a user brings close the identifiers to the authentication components. For example, when two dialysis components carrying the authentication component and the identifier, respectively, are being installed in the dialysis system. The communication between an identifier and an authentication component can also occur when an operation, such as a recharging process, is initiated. The activation of the authentication system such as an RFID system for the signals communicated or received from the RFID components can be one of the first steps in the process of recharging. The communication process between the identifier 120 and the authentication component 110 can also be manually initiated by a user at any stage of the communication process. In non-limiting examples, an identifier 120 may continuously communicate with the authentication component 110 once the communication starts. The communication may be interrupted by a user's command, or may be controlled by an automatic process to stop. For example, when a reusable module is determined not suitable for a recharger, the identifier 120 may stop communicating with the authentication component 110 of the reusable module.

Authentication Components on Dialysis Components

In any embodiment of the first, second, third, or fourth aspects of the invention, authentication components can be affixed onto one or more dialysis components, such as a recharger, a cartridge, a caddy, and a dialyzer. An authentication component may be affixed onto the dialysis component by the manufacturer or a user. Techniques for affixing may involve using certain glue or other adhesive material, taking into account whether the user would like it to be removable, and whether removing the authentication component would cause destruction to the dialysis components.

In general, the manufacturer may want to distinguish installation of the authentication component by non-certified users from that by certified users. The manufacturer may provide specific affixing materials and authentication components only for certified users. In addition, the dialysis component may be able to detect whether the manufacture-certified affixing materials or authentication components are used, based on which the dialysis system can disable any counterfeit products.

Figure 2A:
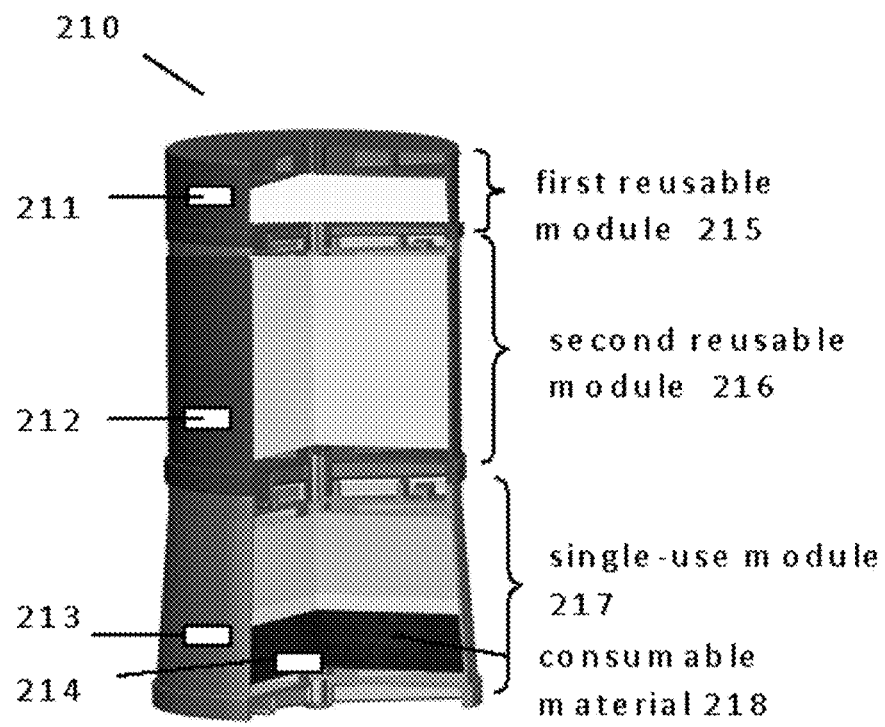
FIGS. 2a-2d show examples of dialysis components and patients having authentication components affixed upon, including a sorbent cartridge (a), a dialyzer (b), a recharger (c) and a caddy (d).
Figure 2B:
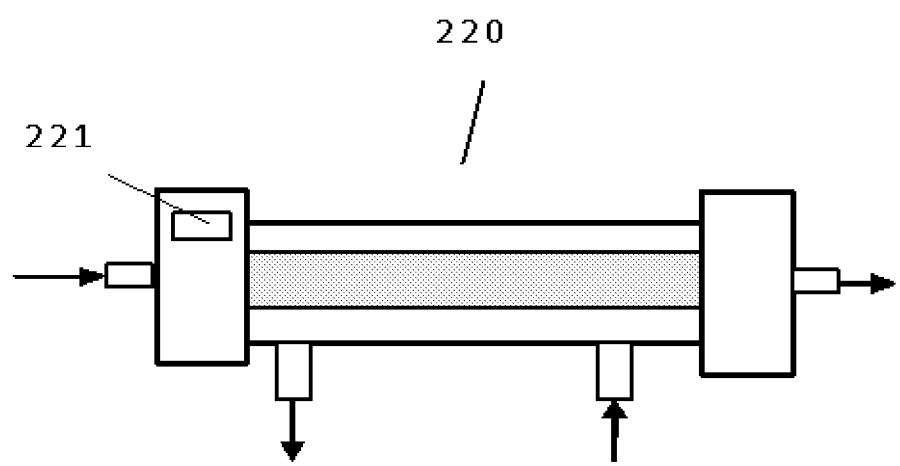
Figure 2C:
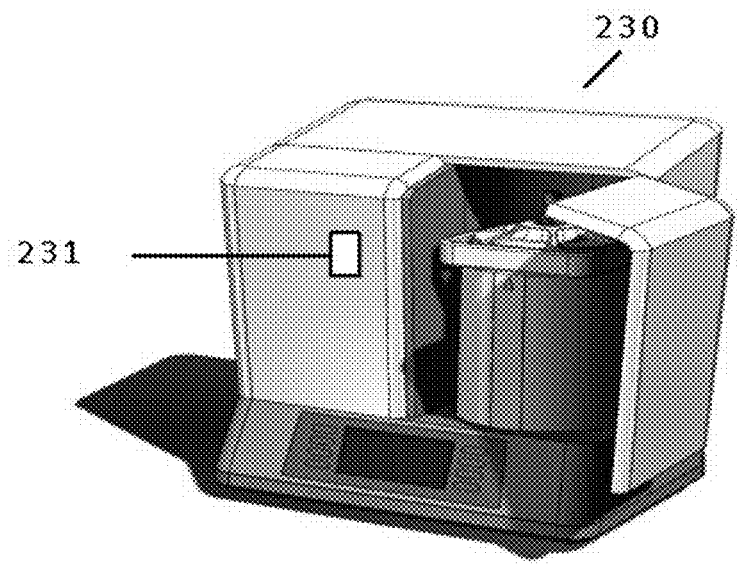
Figure 2D:
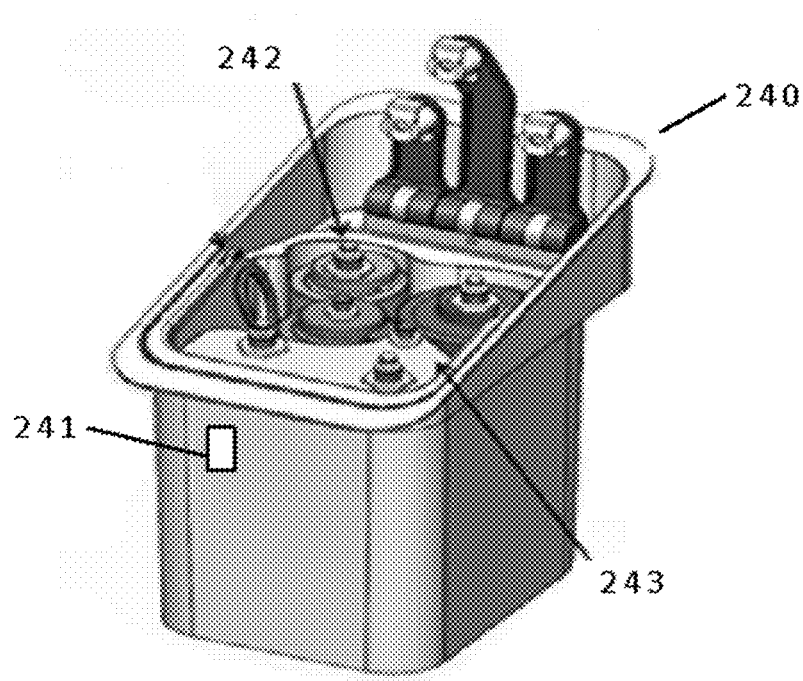

FIGS. 2a-2d show non-limiting examples of different dialysis components having authentication components. FIG. 2a shows a sorbent cartridge 210 for use in sorbent-based dialysis, where authentication components 211, 212, 213, and 214 are attached respectively onto a first reusable module 215, a second reusable module 216, a single-use module 217, and consumable material 218 of the sorbent cartridge 210. FIG. 2b shows a dialyzer 220, where an authentication component 221 is attached to one end of the dialyzer 220. FIG. 2c shows a recharger 230, where an authentication component 231 is attached to the frame of the recharger 230. FIG. 2d shows a caddy 240 having at least one container 242 for infusates and a container for disinfection chemicals, where an authentication component 241 is attached to the frame of the caddy 240. A caddy 240 can have multiple containers for infusates, where each container can have an authentication component attached thereon for information regarding the particular container, for example, different types or concentrations of the infusates (not shown).

Each of the sorbent cartridge 210, the dialyzer 220, the recharger 230, and the caddy 240 may have more than one authentication components, and the authentication components may be attached to different locations of the underlying device. A person skilled in the art will understand that authentication components are not limited to attaching to the dialysis components listed above, and may be attached to patients and other dialysis components, including, but not limited to, circuit tubing, reservoirs, valves, mixers, and heaters.

Figure 3:
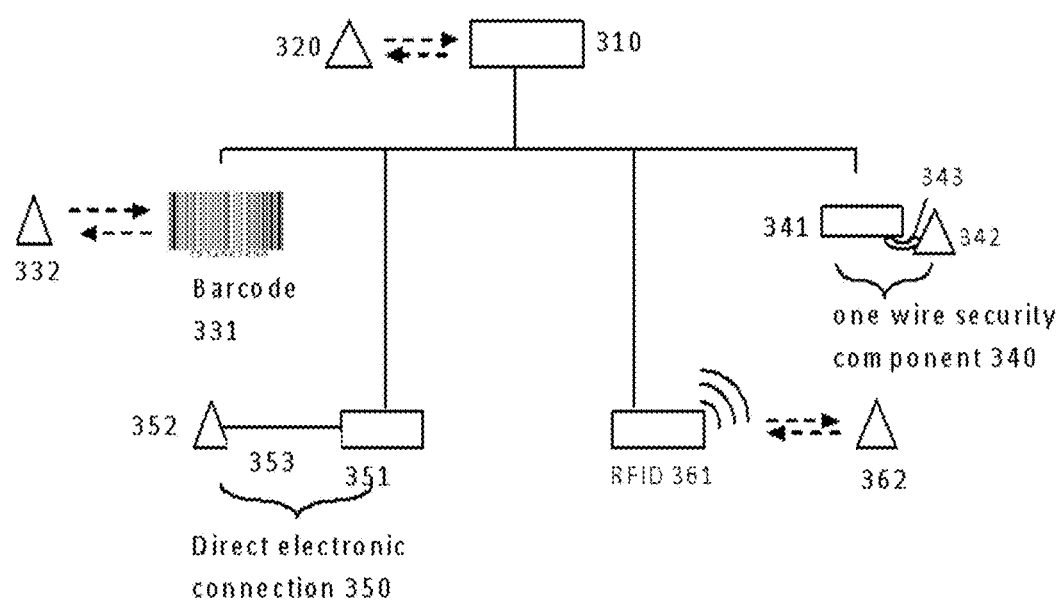
FIG. 3 shows examples of different types of authentication components, including barcode, one-wire security component, direct electronic connection, and an RFID tag.

In any embodiment of the first, second, third, or fourth aspects of the invention, an authentication component can be of any type suitable for identification and authentication purposes known to those skilled in the art. FIG. 3 shows varied forms of the authentication components 310, which are readable by their corresponding readers 320. For example, the authentication system can include any one or more of a bar code 331, a one-wire security system 340, direct electronic communication 350, and a RFID tag 361. A dialysis component can have one or more authentication components 310, and is not limited to a particular type of authentication components. A dialysis component may have a combination of several different types of authentication components.

An authentication system can include a barcode 331 readable by a barcode reader 332. The barcode reader 332 may be permanently affixed to a dialysis component, or the barcode reader 332 may be an external device. The bar code reader 332 can transmit information from the barcode 331 to a processor through wired communication or wirelessly. For example, the authentication component 211 of the first reusable module 215 in FIG. 2 can be the barcode 331, and the information contained in the barcode 331 can be used to determine whether the reusable module 215 is a certified part, matched to the patient, and/or track the usage of the reusable module 215.

An authentication system can include a one wire security component 340 having an identification portion 341 and a reader portion 342, which are connectable by wire 343. The identification portion 341 can be affixed onto one dialysis component, whereas the reader portion 342 can be affixed onto another dialysis component. For example, the identification portion 341 and the reader portion 342 in FIG. 3 can be affixed to the first reusable module 215 and the sorbent cartridge 210 in FIG. 2a, respectively. When the two dialysis components having the identification portion 341 and the reader portion 342 are brought together, a connection can be formed across wire 343. The wire 343 can be attached to any one or both of the identification portion 341 and the reader portion 342, or any one or both of the two dialysis components. The "wired connection" can also be an electrical contact between one or more surfaces of any kind and not require a physical wire to be considered a one wire security component. The identification portion 341 can send an electrical signal to the reader portion 342, across the wire 343. This signal can contain the identification of the corresponding dialysis components and other information. The reader portion 342 can then relay this information to a processor, which can determine whether the dialysis component, such as a reusable module, is certified or exceeds the useful life, track usage of the reusable module, and determine whether the reusable module is matched to the correct patient.

An authentication system can include a direct electronic connection 350 including an authentication component 351, a reader 352 connected by an electronic connection 353. The identification component 351 can be affixed to a dialysis component and the reader 352 can be placed on the dialysis machine. When the dialysis component is connected to the flow path, the reader 352 can read the identification component 351 through the electronic connection 353, allowing information to be transmitted from the identification component 351 to the reader 352.

A person skilled in the art will understand that, direct electronic connection 350 is distinguished from one wire security component 340 in that, the two identification portion 341 and the reader portion 342 in the one wire security component 340 are relatively close to each other and can be considered physically as one component, whereas in the direct electronic connection 350, the authentication component 351 can be read by the reader 352 so long as the dialysis component is connected to the flow path.

An authentication system can include a Radio-frequency identification (RFID) tag, or RFID component 361, readable by a RFID reader 362, which transfers data through the wireless use of radio signals for the purpose of automatically identifying and tracking tags attached to objects. The RFD tags 361 can contain electronically stored information.

RFID Authentication System

Figure 4:
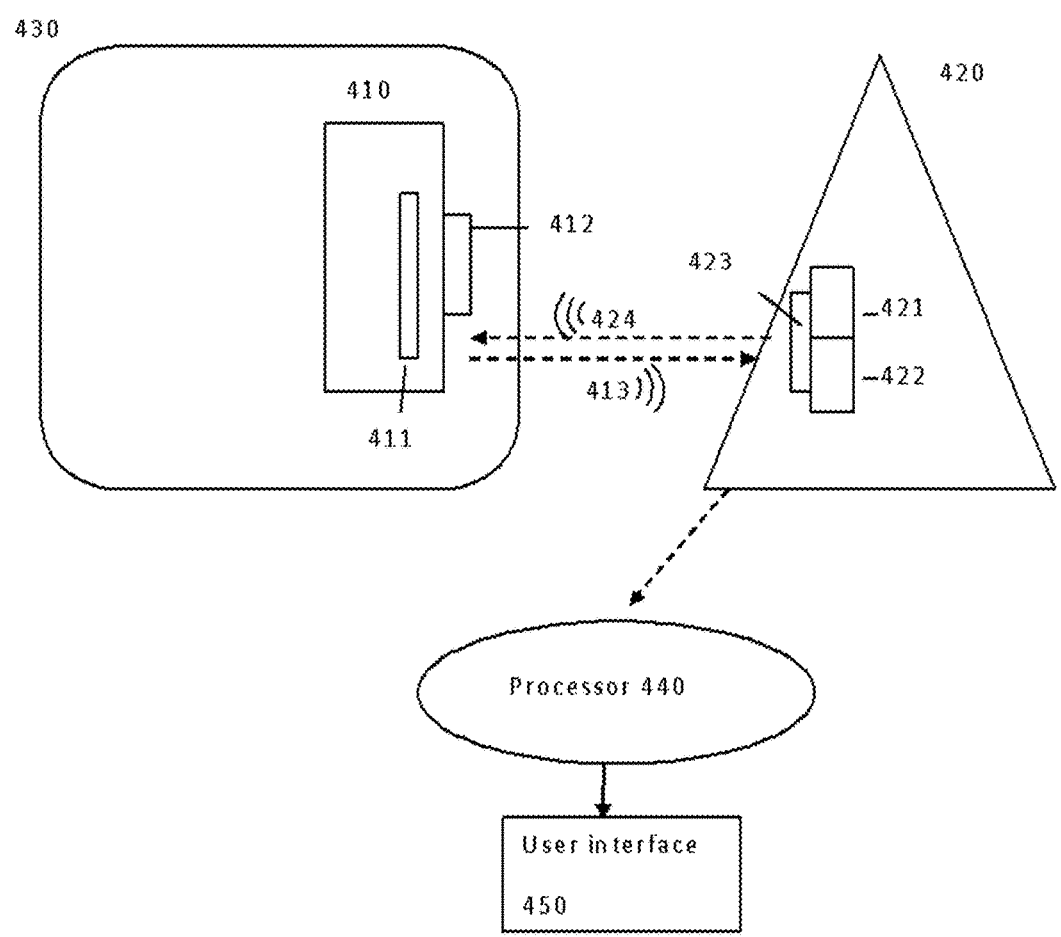
FIG. 4 shows an RFID authentication system have an RFID authentication component and a reader, where data communications occurred therebetween.

FIG. 4 shows in details an RFID authentication system and associated data transferring. The RFID authentication system can include a RFID tag 410 attached to, or integrated into, a dialysis component 430. The RFID tag 410 can comprise a transponder 411 and RF antenna 412. The RFID authentication system can also include a RFID reader 420, which can be disposed within the dialysis system. For example, the RFID reader 420 can be integrated to a second dialysis component different from the dialysis component 430 having the RFID tag 410. Alternatively, the RFID reader 420 may be a separate component that can be held by a user to read the RFID tag 410. The RFID reader 420 can contain an RF source 421 and a detector 422. The RFID tag 410 can be activated when an RF signal 424 is transmitted by the RF source 421 via an RF antenna 423. In response, the RFID tag 410 can transmit back a portion of the original RF signal 424 to the detector 422 via antenna 423 as signal 413. The transponder 411 can carry the identification and other data concerning the dialysis component 430. The information stored in the transponder 413 can determine which portions of the RF signal 424 to reflect back as signal 413. A single antenna 423 can be used by both the source 421 and detector 422. The source 421 and detector 422 can each have separate antennae.

The detector 422 can be capable of detecting the RF signal reflected back by the RFID tag 410 and transmitting the information to a processor 440 via either wireless communication with a wireless authentication component or through wired communication. This information can be used to determine whether the dialysis component 430 is certified, whether is used according to predetermined standards, and any other features or operations regarding the dialysis component 430. The processor 440 can also determine if the dialysis component 430 is matched to the correct patient or a particular dialysis prescription. The processor 440 can optionally comprise a memory device, such as a processor used in a computer. The processor 440 can keep track of the information received from the detector 422.

The processor 440 can optionally include a user interface 450 such as when the processor is being used in a computer. The user interface 450 can be used by a user to interact with the processor 440. Identification and other information stored in the RFID component transponder 411 can be displayed on the user interface 450 and become available to a user. A user may enter a command through the user interface 450 to override an automatic determination made by the processor 440. For example, when the processor 440 automatically disables the system due to non-certified parts, a user may want to reactivate the system when the non-certified parts are determined to be newly certified or become usable for other reasons The RFID component 410 may be affixed to the dialysis component 430 by using an adhesive. The adhesive selected would ideally be an adhesive that will not significantly degrade with use or time. This will keep the RFID component 410 from falling off during use, shipping, or handling. Alternatively, the RFID component 440 may be embedded within the dialysis component 430, for example, in the housing of a reusable module of a sorbent cartridge, which can prevent tampering with the RFID component 440. Other methods known to the art can also be used for affixing the RFID tag 440.

The RFID component 440 may be active or passive. In a passive device, the incoming RF signal 424 provides enough power for the RFID component 440 to operate, thereby eliminating the need for an additional power source. RFID component 440 may have its own power source (not shown) and operate as an active component, which allows a more powerful return signal be returned and is capable of being used in the next dialysis session.

Figure 5:
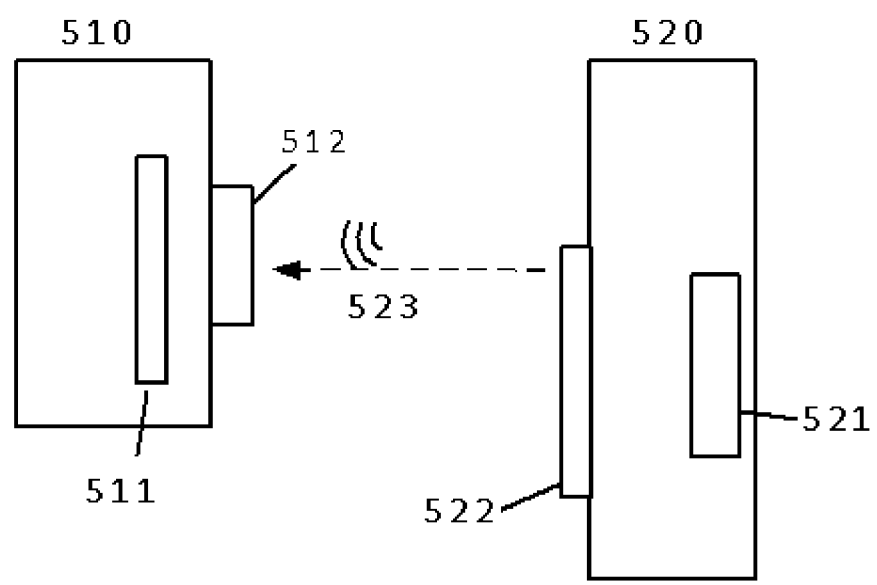
FIG. 5 shows a writer in the authentication system having an RFID authentication component.

In any embodiment of the first, second, third, or fourth aspects of the invention, the RFID system can include an authentication component that is both readable and writable. FIG. 5 shows an RFID system including a RFID component 510, which is both readable and writable. The RFID system in FIG. 5 can further include a writer 520 to write on the RFID component 510. The writer 520 may be fixed to a dialysis component, and may also be a device separated from any dialysis components.

The RFID component 510 includes a transponder 511 and an antenna 512. The RFID writer 520 comprises a source 521 and an antenna 522. When the writer 520 receives an input directing the writer 520 to write to the RFID component 510, the source 521 generates an RFID signal 523 that is transmitted by the antenna 522. The signal 523 is received by the antenna 512 on the RFID component 510, and transmitted to the transponder 511. The transponder 511 then changes specific information stored within the transponder circuitry (not shown). The changed information can subsequently be included and become readable in the RFID component 510.

RFID technology can be used to protect patient safety and improve treatment efficiency by matching dialysis components to a patient. For example, the RFID component 510 can track the number of recharges of a reusable module, verifying that the recharge process is initiated within an acceptable time limit from the last treatment session, and verifying that a new cartridge is not being recharged. In a non-limiting example, a user can disable or dispose of a reusable module prior to the module becoming overused based on the written information in the RFID component 510, and thus avoid degradation of the therapy. The RFID technology in the dialysis treatment is not limited to the above described uses.

The RFID component 510 can be any known type of RFID tag or commercially available RFID tag, such as a TIRIS Tag-It™ smart label made by Texas Instruments. The Tag-It™ smart label provides for an ultra-thin form that can be laminated into a paper or plastic label, allowing the smart label to be easily attached to a dialysis component or other objects without taking extra space. Other known labels in the art can also be used by the authentication system for managing the dialysis therapy.

Figure 6:
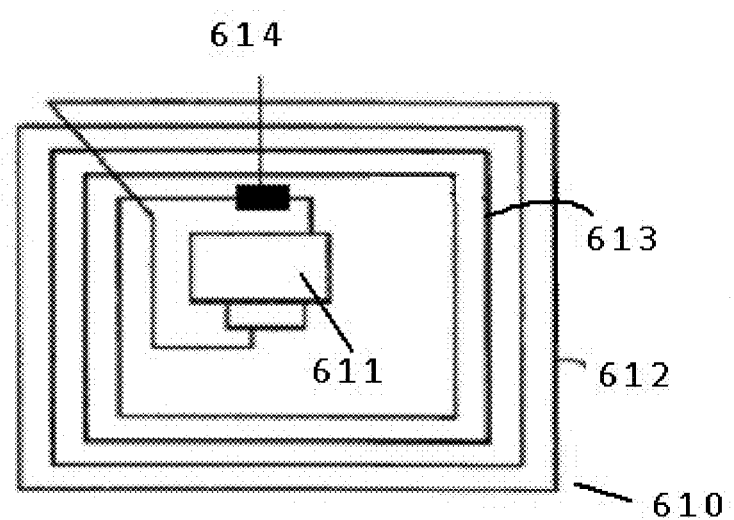
FIG. 6 shows an RFID tag having a microchip for storing memory.

In any embodiment of the first, second, third, or fourth aspects of the invention, a microchip may be included in a RFID component for larger amounts of information to be stored and transmitted. FIG. 6 shows a RFID component 610 having a transponder 611, an antenna 612, and a microchip 614 on an integrated circuit 613. The microchip 614 can contain information about the history of the product, including manufacturer, date of manufacture, number of uses, and other relevant information. The information on the microchip 614 can be sent to a RFID reader. Using the microchip 614, such as a Maxim chip, in the RFID component 610, the memory can be fully integrated into the RFID component 610, and therefore eliminates the need for an external processor to write to the RFID component 610.

Figure 7:
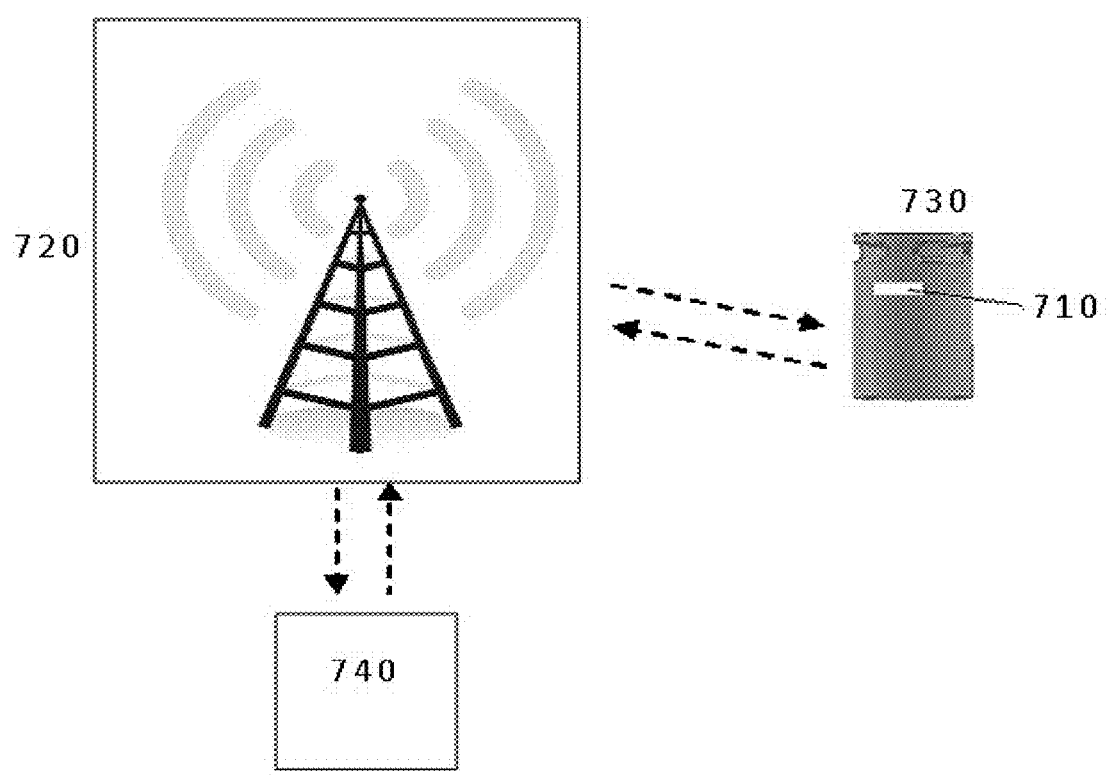
FIG. 7 shows remote data transferring of an RFID authentication system.

In any embodiment of the first, second, third, or fourth aspects of the invention, relevant data can be remotely stored and accessed by using RFID components that can respond to a RFID reader's query. Data contained in the RFID components can be collected and transferred to a processor through an RFID reader. FIG. 7 shows that a user 740 can send a request to a mobile host 720 to track a particular RFID tag 710 affixed on a dialysis component 730. In response, the mobile host 720 can then track the RFID tag 710. When the mobile host 720 detects the RFID tag 710 within its network, the host 720 can obtain the location of the RFID tag 710. Information in the RFID tag 710 can be stored, along with a time stamp, in the host 720, and become available to the user 740.

RFID system can track dialysis components in locations where cellular networks are available. Distribution of dialysis components, such as the reusable modules, can be easily tracked by using the RFID systems. In non-limiting examples, clinicians can remotely monitor the dialysis therapy through the RFID system, so that professional assistance can be available in a service setting outside of a clinic dialysis center, such as at a patient's home or a dialysis mobile station.

A dialysis center or clinic refers to a permanent location providing dialysis to patients. The dialysis center or dialysis clinic may employ doctors, nurses, or dialysis technicians to provide dialysis for multiple patients simultaneously. The dialysis clinics can be any size, ranging from clinics designed for one or two patients to clinics designed for dozens of patients or more.

At home dialysis refers to dialysis carried out by a user in his or her residence or other building outside of a clinical setting. At home dialysis may occur under hospice care or other medical supervision of doctors, nurses, or clinicians, but these are not always necessary. However, at-home encompasses many other types of homes or out-of-clinic settings including homes and settings in less developed areas. The RFID authentication system or other types of the authentication systems can be used in those areas, countries, or locales where support infrastructure, including a data network, is at a reduced level.

A mobile setting for dialysis refers to a movable dialysis setting. A mobile setting may comprise a mobile dialysis unit dispatched to one or more locations to provide dialysis to patients. The dialysis unit may be a large unit, capable of providing dialysis for multiple patients in a central location, or may be a smaller unit, capable of providing dialysis for only one or a few patients in a particular location. The mobile dialysis unit may arrive at a location and set up a "pop-up" dialysis clinic, or a dialysis clinic that is only in a particular location for a brief time. Often, a mobile dialysis unit may have little permanent infrastructure or support, such as lacking a data network established similar as that in a clinic dialysis center.

A person skilled in the art will understand that the dialysis components can be tracked using any other wireless technology. Non-limiting examples of possible wireless technology include Bluetooth, Wi-Fi, LTE, WiMax or any other wireless technology known to those of ordinary skill including proprietary wireless technologies.

Patient Information Storage Device

In any embodiment of the first, second, third, or fourth aspects of the invention, RFID authentication components can be used as a patient information storage device. The patient information storage device can contain one or more of the following information: the patient's name, patient prescription, last patient blood analysis, weight, prior session information, such as when were prior sessions conducted, how long for prior sessions last, alarms in prior sessions, cartridge size information, other parameters needed for performance optimization, including information relevant to the patient's dialysis treatment such as last blood analysis. For example, patient information may include session parameters, such as date of last session, duration of last session, and other conditions regarding last session.

Figure 8:
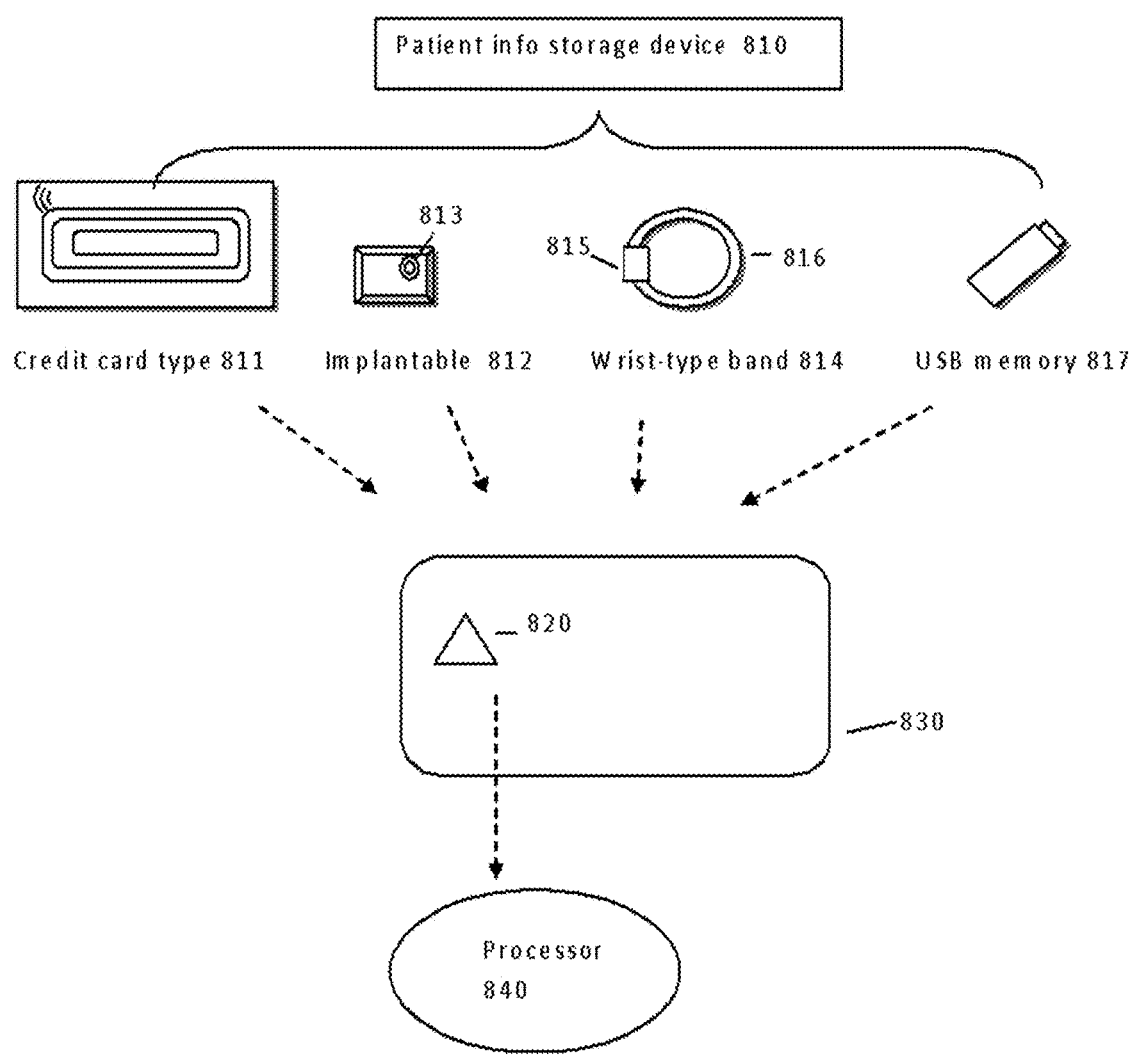
FIG. 8 shows a patient information storage device containing RFID authentication components.

FIG. 8 shows examples of patient information storage device 810, which can be any types of RFID components and other types of the authentication components, such as a USB memory stick 817. However, the RFID technology is often used as a patient information storage device due to the advantages known to the art. The RFID patient information storage device 810 can be made as a RFID badge or card-like device, RFID card 811, an implantable chip 812 having an optional sensor 813, or a wrist-band device 814 having an RIFD tag 815 and a wrist band 816. The RFID patient information storage device 810, for example, a credit card sized device such as the RFID card 811, which can contain embedded memory and with an RFID type communication, enables the implementation of the therapy optimization idea in a more efficient way. The RFID nature of the RFID card 811 can be utilized to wirelessly and effortlessly transfer data back and forth between the memory device before and after each dialysis. However, other devices such as the USB memory stick 817 could also be used for the therapy optimization.

In any embodiment of the first, second, third, or fourth aspects of the invention, the RFID components of the patient information storage device can consist of a RFID chip and a Memory Chip bonded in a "smartcard" package. Integrated circuits embedded in the smartcard can store and process data, where the data can be transferred back and forth with a terminal via RFID signals. The smartcard design is not limited to a RFID tag in the patient information storage device 810. A person skilled in the art will understand that the smart card RFID may be utilized in any dialysis components including consumables.

The implantable RFID tag 812 can be implanted into a patient, for example, in the fistula of the patient. The fistula is an abnormal connection between two epithelialized surfaces, such as blood vessels, where often vascular surgery needs to be performed. The patient information can be updated to incorporate real-time measurements of the patient's parameters through an integrated sensor 813 that can measure interest parameters of the body environment. The implantable RFID tag 812 can provide clinicians with the most updated information of the patient.

In non-limiting examples, the dialysis system can read the patient information storage device 810, and obtain the information stored therein for the therapy optimization. The dialysis system can read in the patient name from the patient information storage device 810, and the patient name can then be used to compare against the rechargeable cartridge to ensure that it matches the patient name. The patient name can be used for determining whether other dialysis components match the patient name, such as a dialyzer. The dialysis system can also read in the patient's description from the patient information storage device 810, and transfer the patient prescription to the dialysis machine for proper setting.

In any embodiment of the first, second, third, or fourth aspects of the invention the patient information storage devices 810 can store prior session data including those for multiple sessions. The prior session data stored in the patient storage devices 810 can be used by the dialysis machine and/or the clinician to optimize setup of the machine/dialysis session to improve the optimal therapy in the shortest period of time. The session parameters can include alarms regarding, for example, the patient's blood pressure, blood flow, and ammonia breakthrough, which are detected during prior sessions. The session parameter information may also include duration of last session or other prior sessions, and date of last session or other prior sessions.

In any embodiment of the first, second, third, or fourth aspects of the present invention, the patient information regarding the alarms in the prior sessions can be utilized by the clinician to adjust the dialysis machine, and can also be utilized directly by the dialysis machine for an automatic adjustment. Either way, the patient information including the prior session information can be utilized to adapt the therapy for an optimized outcome. Non-limiting examples of the adjustment include adapting blood flow rates to reduce hypotensive episodes or blood flow alarms. The ammonia breakthrough alarm or a pattern of the ammonia breakthrough can also be detected, which can be a signal to the clinician to utilize a larger capacity cartridge.

The patient information storage device 810 may carry any relevant information useful for therapy optimization of the dialysis treatment. For example, the patient information storage device 810 can store event alarms during the past treatment, such as alarms with respect to the patient's blood pressure or blood flow rate going beyond the safety range. Non-limiting examples can include hypotensive event alarms and hypertensive event alarms. The clinician may consider adapting blood flow rates to reduce hypertensive episodes or blood flow alarms. Information from past sessions, such as the hypotensive event alarms, can also be extracted from the RFID patient storage device, and can be used to adjust the therapy parameters, such as blood flow, UF rate, and UF profile. The alarm signals may be also regard the clearance of blood ammonia during the dialysis treatment. If an ammonium breakthrough is detected or a pattern of the break through is detected with a particular patient, the clinician may consider adjust settings of the dialysis system or utilizing a larger size of cartridge.

In any embodiment of the first, second, third, or fourth aspects of the invention, the patient storage device 810 can be updated to store newly measured data of a particular patient. The data may come from a sensor integrated in the patient storage device 810, such as the sensor 813 in the implantable RFID tag 812, or from remote resources. For example, a scale can be set up to wirelessly write the patient's RFID card 811. Other devices that are able to generate measurements may also write to the RFID card 811 or any other authentication components. Recording the patient information through automatic data transferring via the RFID technology enables real-time recording and greatly reduces human errors occurred in manual transcription. A person skilled in the art will understand that other types of authentication components, such as the USB memory stick 817 can also be used to record updated information of the patient.

The patient information storage device 810 can improve the overall patient management. Conventionally, when patients come in for dialysis, they are weighed, and the weight information is manually utilized to set the UF amount and rate. In any embodiment of the first, second, third, or fourth aspects of the invention, the patient information storage device 810, such as the RFID card 811, can be used to record updated information of the patient, including the weight information. For example, the scale can be setup to wirelessly write to the RFID card 811. The updated information of the patient's weight can then be utilized by the dialysis machine to automatically set the UF amount and rate. The use of RFID technology in the patient management greatly reduces the burden of manual record keeping, thereby mitigating the chance of error.

In non-limiting examples, the patient information storage device 810 can be read by an identifier or a reader 820. The reader 820 may be attached or integrated to a dialysis component 830. The reader 820 may be a device separated from any dialysis components. The reader 820 may store relevant information of the corresponding dialysis component 830. The reader 820 may be a smartcard type device. Once receiving the patient information, the reader 820 or the processor 840 can determine whether or not the dialysis component 830 and its setting are suitable for the patient. For example, the reader 820 contains information of the consumable material, and the authentication process in the reader 820 or the processor 840 determines whether the consumable material matches the right patient.

The patient information storage device 810, especially those of RFID technology, can provide more convenience for clinicians and patients. For example, the session performance information can be accessed when data network of the clinic center is not available. Portable devices can be used and further adjusted outside of the clinic center, based on the patient information in the patient information storage device 810. The patient information storage device 810 also improves the overall patient management by clinicians, as patient information can be available and used regardless of where the therapy occurs.

The RFID patient storage device and other types of the authentication components can be used wirelessly and effortlessly to transfer data back and forth between memory devices before and after each dialysis, and sometimes during the dialysis, therefore significantly increasing the flexibility of using the dialysis system. The therapy optimization can be possible by using the RFID technology even in remote areas where the center network is not available, or at the time when the center network does not function well.

In any embodiment of the first, second, third, or fourth aspects of the invention, the patient information storage device 810 can provide session performance information to the physician to help manage the patient. The RFID authentication system, for example, when using the RFID card with the embedded memory, may not depend on the center having a network. The dialysis device across dialysis centers can become more portable and flexible for use.

Figure 9:
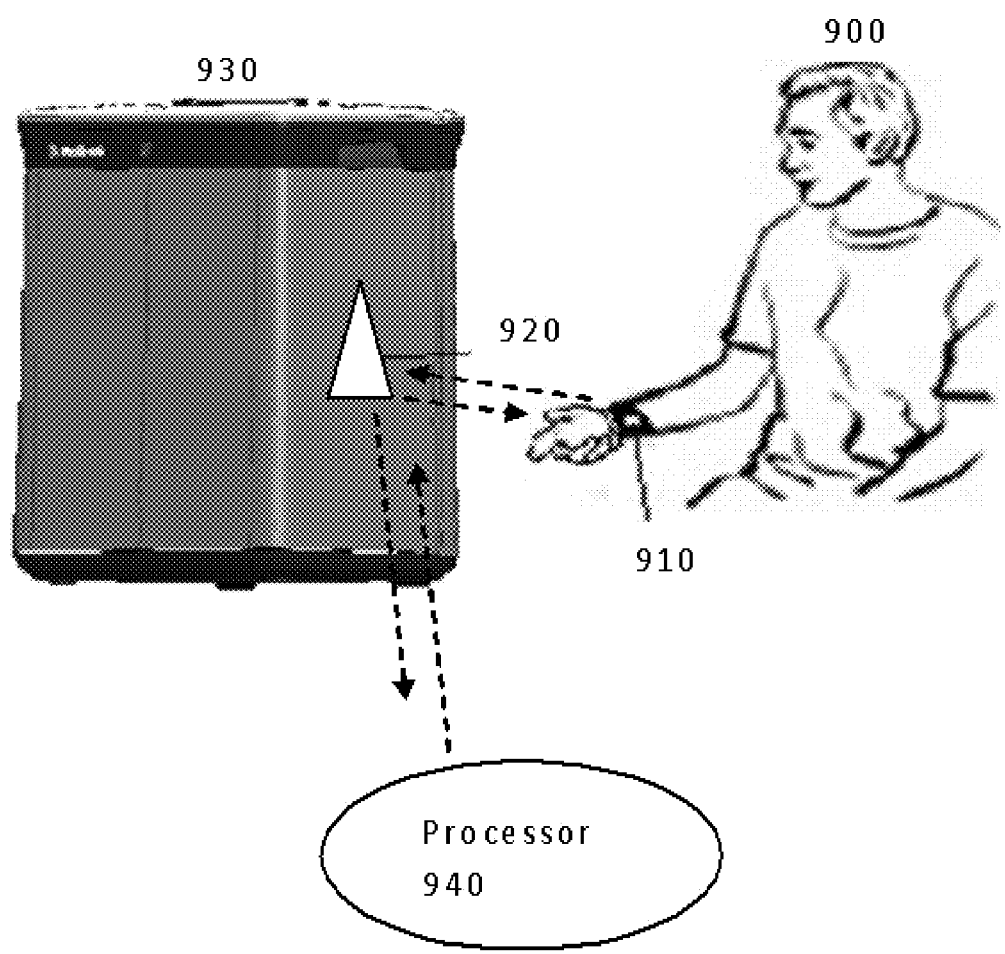
FIG. 9 shows a wrist-band RFID component attached to a patient, the information contained therein is readable by a reader of a dialysis component.

FIG. 9 shows a non-limiting example of utilizing the patent information storage device, a wrist-band RFID 910, in the dialysis therapy of a patient 900. The wrist-band RFID 910 can be brought close enough by the patient 900 to a RFID reader 920. The reader 920 may be the same reader as is used for the dialysis components or a different reader separated from the dialysis components. For instance, the reader 920 may be attached to a dialysis cabinet 930. The patient 900 can carry any types of the patient information storage device, including, but not limited to those in FIG. 8.

Information from the patient's information storage device, such as the RFID wrist-band 910, can be transmitted to the processor 940, so that a user of the processor 940, such as a clinician, can assure the correct components to be used for the specific patient 900.

The patient information storage device can contain other information besides simple identification of the patient. For example, the wrist-band RFID 910 can contain information regarding the patient's prescription, the date of the patient's last treatment, or any other information pertaining to the individual. Alternatively, the patient's wrist-band RFID 910 may only contain identification information. Information in the patient wrist-band RFID 910 can be read and stored in the processor 940 having a memory component, such as updated information of the dates of the patient's dialysis sessions and the patient's prescription.

Figure 10:
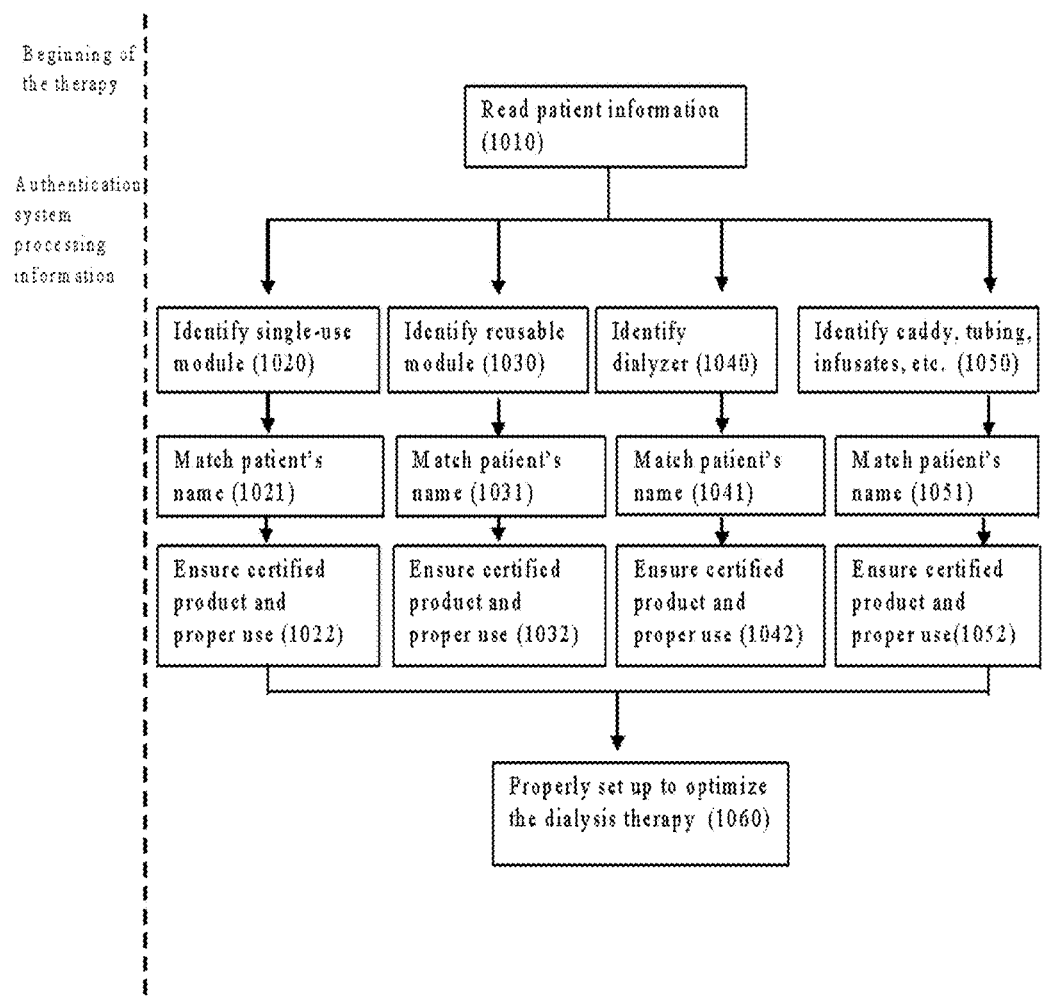
FIG. 10 shows diagrams of a patient information storage device and other authentication components used for optimized setting of the dialysis machine.

FIG. 10 shows steps of authentication systems processing information at beginning of the dialysis therapy. The authentication system can read patient information at step 1010. Patient information can include the patient identification, dialysis prescription, and treatment history. After identifying the patient, the authentication system can identify the single-use or non-reusable module at step 1020 by reading an authentication component attached thereon. The authentication system can confirm that the non-reusable module matches the patient's name at step 1021, and determine that the non-reusable module is a certified component and is properly used at step 1022. Proper usage may concern whether the non-reusable module has not been used, and is within its expiration date. The authentication system can also identify the reusable module at step 1030 by reading an authentication component attached thereon. The authentication system can confirm that the reusable module matches the patient identification at step 1031, the patient identification can be in any form, such as the patient's name or a serial number representing the particular patient. The authentication system can determine at step 1032 that the reusable module is a certified component, that the reusable module has been properly recharged, and that the reusable modules within the allowable number of times for safe recharging. The authentication system is not limited to making determinations described above.

In any embodiment of the first, second, third, or fourth aspects of the invention, the authentication system can identify the dialyzer at step 1040, confirm that the dialyzer matches the patient's information at step 1041, and determine at step 1042 that the dialyzer is used properly. Additionally, the system can identify other dialysis components such as caddies, circuit/blood tubing, infusates, and other components or consumables at step 1050, confirm that, these dialysis components, match the correct patient at step 1051, and determine at step 1052 that they are certified products and are used properly, for example, the caddy contains infusates filled correctly to match a particular patient.

In non-limiting examples, steps associated with different dialysis components may not be necessarily following a particular order as indicated by the step numbers in FIG. 10. One dialysis component can be identified prior to other dialysis components and have the information subsequently processed before starting the dialysis. Multiple dialysis components can also be identified and determined simultaneously when the information can be read and processed simultaneously, for example, by different readers and processors.

In any embodiment of the first, second, third, or fourth aspects of the invention, information regarding the single use module, the reusable module, the dialyzer and other dialysis components can be utilized for optimized settings of the dialysis system at step 1060. The reusable module can be disabled by the authentication system due to improper usage, for example, when the reusable module exceeds a limit number of recharging. Optimized setting of the dialysis system may also include adjust fluid flowing rate to match the expectation corresponding to the patient's prescription. The patient's prescription can be transferred as part of the patient information from the patient information storage device to a processor controlling the dialysis system. The settings of the dialysis system can also remain unchanged when the dialysis components are determined to match the patient information, are certified product and are used properly or according to any suitable standards decided by a user.

In non-limiting examples, one or more dialysis components may need to match to a particular patient, including, but not limited to, sorbent cartridges, dialyzers, and other consumables, such as infusates and blood tubing set. In non-limiting examples, one or more dialysis components may not need to meet the particular patient for therapy optimization. For example, a reprocessing program or a recharging program of sorbent modules may be universal to different patients. The information used by a recharger or a reprocessor can include when the modules were last used, how many uses, use before date, cartridge, and other relevant information, which does not necessarily include a patient's name or description. The information used by a recharger or a reprocessor can also include a patient's information, for example, when sorbent modules need to be recharged/reprocessed to regain the functional capacity that matches the particular patient.

In any embodiment of the first, second, third, or fourth aspects of the invention, the dialysis system can contain a reader on the console, to read a sorbent cartridge, and determine whether there is a valid and recharged cartridge that matches the patient name and cartridge size. The dialysis system can also extract information of past sessions from the RFID components, such as the patient information storage device or those attached to a dialysis component. The past session information can be hypertensive event alarms or hypotensive event alarms, which can be used to adjust the therapy parameters, including, but not limited to blood flow, UF rate, and UF profile.

Figure 11:
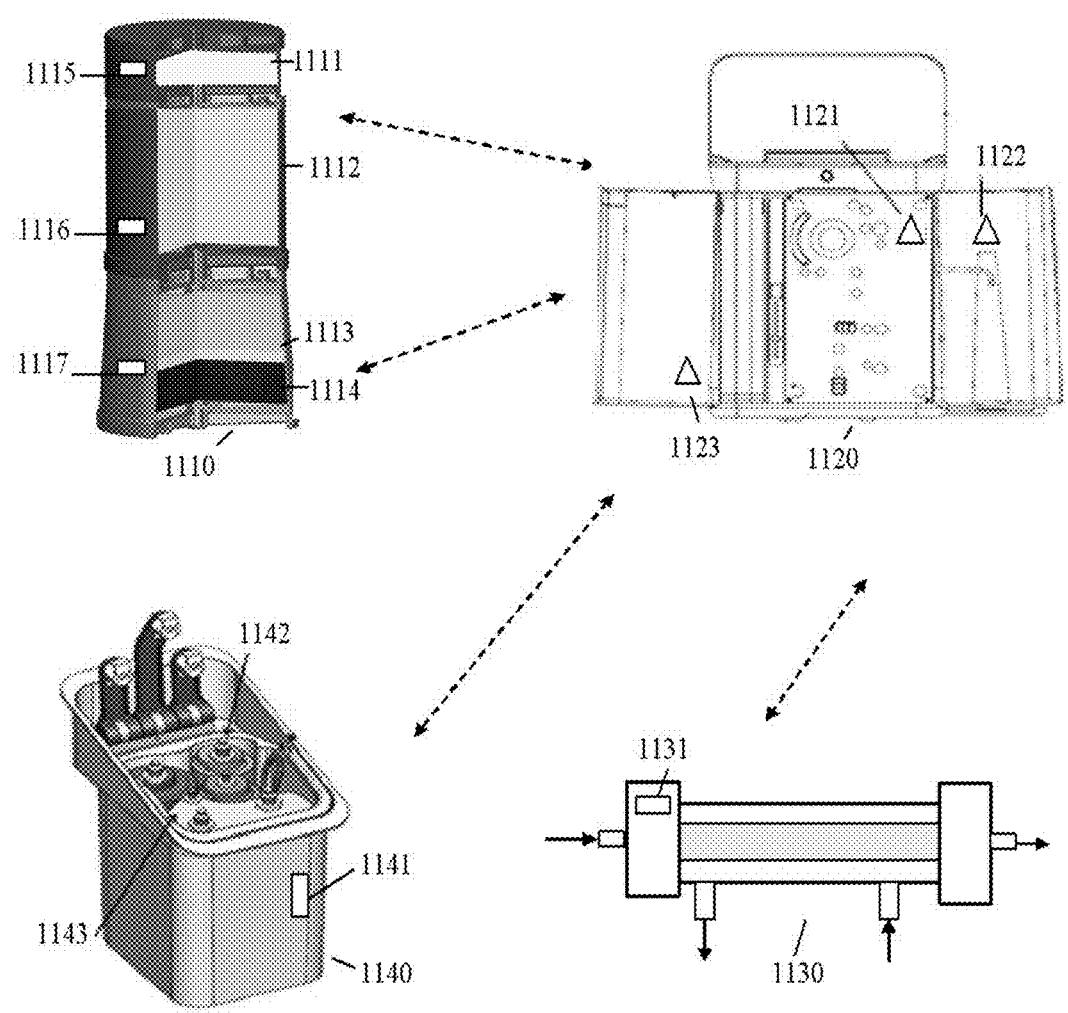
FIG. 11 shows a dialysis cabinet having one or more readers to read authentication components on a cartridge, a caddy, and a dialyzer.

FIG. 11 shows an authentication system concerning a dialysis cabinet 1120 and multiple other dialysis components including a sorbent cartridge 1110, a dialyzer 1130, and a caddy 1140. The dialysis cabinet 1120 can have a first reader 1121, a second reader 1122, and a third reader 1123, which can read authentication components, such as RFID tags, attached to the dialysis components, including, but not limited to, sorbent cartridges, rechargers, dialyzers, and caddies. These readers may each read RFID tags attached to a particular type of dialysis component, and may also be able to read RFID tags attached to different dialysis components. The first, second, and third readers 1121-1123 can be provided at different places of the dialysis cabinet 1120 to correspond to the one or more target dialysis components. The dialysis component 1120 can have one or more readers. The dialysis cabinet 1120 may only need one reader that can read all of the RFID tags attached to the different dialysis components. A reader can also be separated from the dialysis cabinet 1120.

FIG. 11 shows a sorbent-cartridge 1110 that contains multi-use modules 1111 and 1112 having rechargeable materials and a single-use or consumable module 1113 having consumable materials 1114. The authentication components such as RFID tags 1115, 1116, and 1117 can be attached to the multi-use modules 1111 and 1112 and single-use module 1113, respectively. The RFID tags 1115, 1116, and 1117 can be read by one or more readers located in a dialysis cabinet 1120, such as the first reader 1121 and the second reader 1122. The first reader 1121 can read and distinguish RFID tags 1115 and 1116 simultaneously. Alternatively, an additional reader (not shown) may be included in the dialysis cabinet 1120 to specifically read one of the multi-use modules.

The authentication system in FIG. 11 can process information of cartridge size and performance of the multi-use modules 1111 and 1112. For example, the RFID tag may contain information regarding efficiency of the sorbent cartridge 1110 or the modules 1111-1113 contained therein for removing specific solutes from the spent dialysate, or the binding capacity of specific sorbent materials within the modules 1111-1113, or variations of chemical performance of consumable materials. The authentication system can determine the length of time that has elapsed since the reusable module 1111 or 1112 has been used. This information can be advantageously used as an expiration or time limit to avoid possible contamination from microbial or fungal growth in a recharging/reprocessing unit or step.

In any embodiment of the first, second, third, or fourth aspects of the invention, both reusable modules and non-reusable modules can be read when connected together and inserted into the dialysis cabinet. For example, the non-reusable module 1113 of the sorbent cartridge 1110 can be read by the reader 1122 in the dialysis cabinet 1120. The readers 1121 and 1122 can cooperatively read the required information or read independently. Additionally, at least one of the readers 1121 and 1122 or any additional reader can read the RFID tag placed in the consumable material 1114.

FIG. 11 also shows a dialyzer 1130 having an RFID tag 1131. When the dialyzer 1130 is placed in the dialysis cabinet 1120, the reader 1122 can read the dialyzer RFID tag 1131. The dialyzer RFID tag 1131 may also be read by any suitable reader, such as reader 1121 or reader 1122, placed in the dialysis cabinet 1120, or a reader separated from the dialysis cabinet 1120 (not shown). In any embodiment of the first, second, third, or fourth aspects of the invention, the authentication system can confirm that the dialyzer 1130 matches the patient identification, that the dialyzer 1130 is certified, that the dialyzer 1130 has been recharged and is ready for use, that the dialyzer 1130 is within the allowable number of safety uses, and that it has not been too long between uses of the dialyzer 1130.

FIG. 11 shows a caddy 1140 having an infusate container 1142, a disinfection container 1143, and an RFID tag 1141. When the caddy 1140 is placed close to or inside the dialysis cabinet 1120, the RFID tag 1141 can be read by at least one reader of the dialysis cabinet 1120, such as reader 1123, or a reader separated from the dialysis cabinet 1120 (not shown). The dialysis system can confirm one or more of the following: the caddy 1140 matches the patient identification, the caddy 1140 is certified, the caddy 1140 has been filled according to the patient's prescription and is ready for use, the caddy 1140 is within the allowable number of safety uses, and has not been stored too long between uses of the caddy 1140. The authentication system may also determine whether the caddy 1140 is hooked up properly in the dialysis cabinet 1120.

The authentication system is not limited to making determinations on the features in FIGS. 10 and 11. The RFID tags attached to the dialysis components can be read simultaneously, and can also be read separately in any order, by the one or more readers in the authentication system. In non-limiting examples, determination on one dialysis component may have influence on processing information of other dialysis components. For example, if the dialyzer 1130 is determined to be a noncertified product, the authentication system may not proceed with other dialysis components until a user takes further action, such as confirming the use of the noncertified product, or replacing with a certified dialyzer. The authentication system of FIG. 11 can also read each of the RFID tags independently to make determinations concerning all of the RFID-tagged dialysis components at once.

Figure 12:
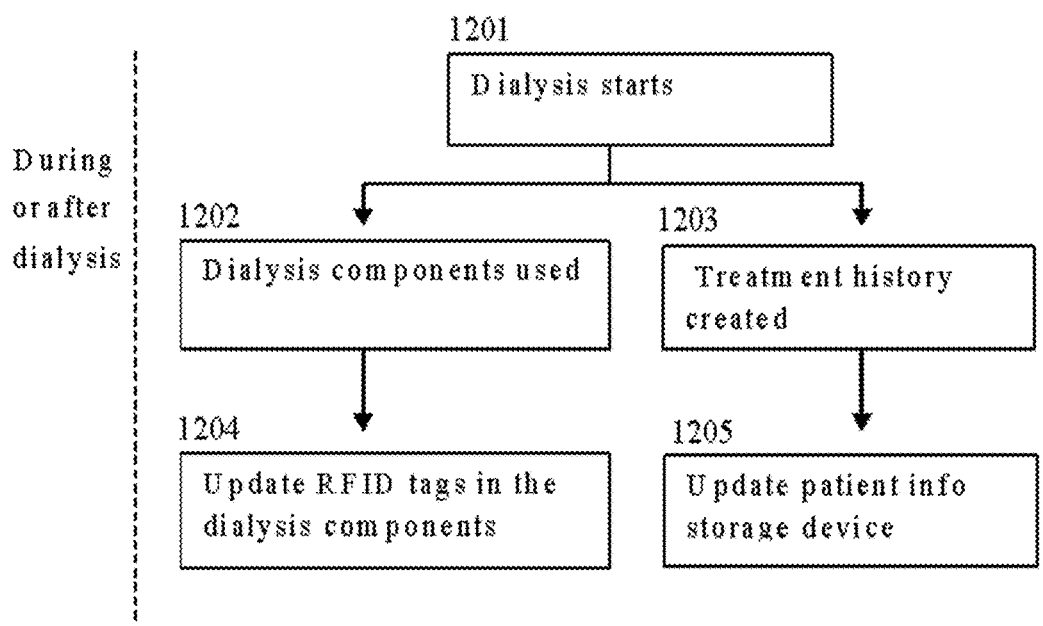
FIG. 12 shows diagrams of updating information of RFID components during or after dialysis.

In any embodiment of the first, second, third, or fourth aspects of the invention, the writable RFID tags or system database can be updated during or after the dialysis. FIG. 12 shows that the dialysis starts at step 1201, and the dialysis components are subsequently used at step 1202. Events occurred during the dialysis session can be monitored as part of the treatment history for the particular patient at step 1203, including events occurred during the dialysis session, such as alarms of blood pressure changes.

Information regarding the recent usage of the dialysis components can be saved in the corresponding RFID tags of the dialysis components at step 1204 in FIG. 12. For example, in FIG. 11, the RFID tag 1117 on the non-reusable module 1113 can be updated to show that the non-reusable module 1113 has been used. The RFID tag 1115 on reusable module 1112 can be updated to show that the reusable module 1112 has been used for one more time, and that the reusable module 1112 is currently not recharged. The RFID tag 1131 on dialyzer 1130 can also be updated to show that the dialyzer 1130 has been used and that the dialyzer 1130 is currently useable. Other dialysis components such as circuit tubing and consumable materials can also be updated by saving newly generated information regarding their respective usage in the corresponding RFID tags or other authentication components.

The authentication system can also update the patient information at step 1205 of FIG. 12, during or after the dialysis session. For example, the patient information including the most recent treatment history can be saved in the patient information storage device, such as the wristband RFID 910 in FIG. 9. In non-limiting examples, updated information of the dialysis components can also be saved in a reader or a processor that is used for the current or next dialysis session.

Figure 13:
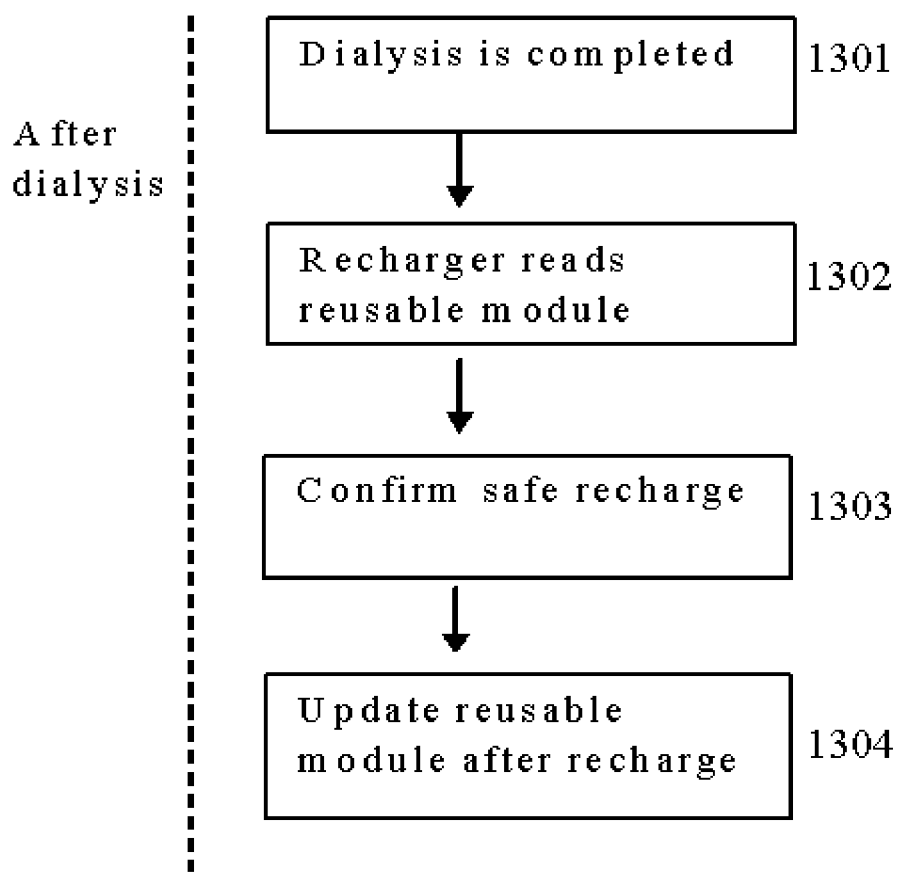
FIG. 13 show diagrams of an authentication system managing a recharging process after dialysis.

FIG. 13 outlines a use of managing recharging of rechargeable dialysis components. FIG. 13 shows that, after the dialysis is completed at step 1301, the rechargeable component may be taken from the dialysis machine for recharging. At step 1302, the RFID tag attached to the rechargeable component can be read by a reader attached to the recharger. The recharger then can confirm that the rechargeable component can be safely recharged at step 1303 before recharging. Once the recharging is done, the recharger can optionally update information of the RFID tag at step 1304 for the rechargeable component by incorporating the most recent information of recharge.

Figure 14:
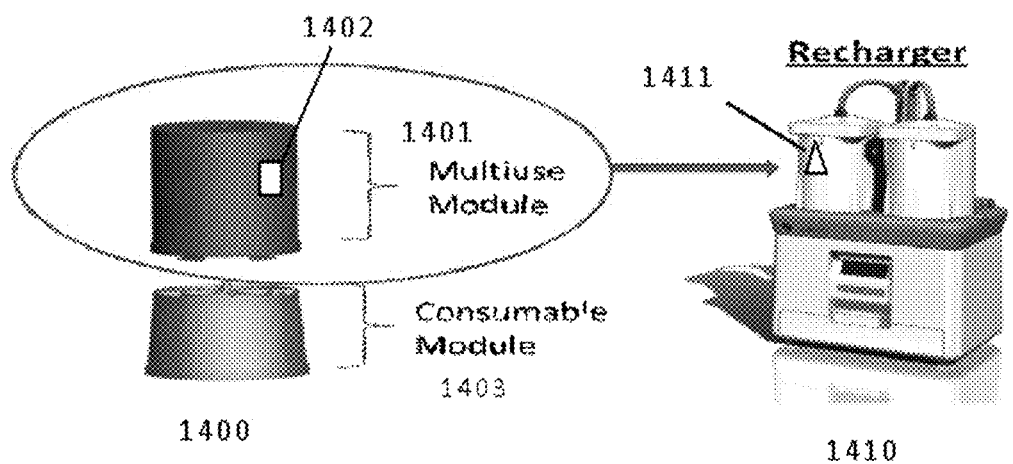
FIG. 14 shows an example of an authentication system having an authentication component on a reusable module and an identifier on a recharger.

In non-limiting examples, the reusable sorbent cartridge 1400 in FIG. 14 may be taken from the dialysis machine to a recharger 1410. The reusable sorbent cartridge 1400 also contains a consumable module 1403 that is not subject to recharging. The consumable module 1403 contains an authentication component that may not be readable by the reader of the recharger 1410, or the recharger 1410 can determine that the consumable module 1400 is not rechargeable (not shown). Before the recharging process starts, the reader 1411 of the recharger 1410 can read the RFID tag 1402 on the reusable module 1401 to confirm that the reusable module 1402 is in a used state, and that the reusable module 1402 is within the number of times allowed for safe recharging. The reusable module 1401 can be recharged, and the recharger 1410 can write to the RFID tag 1402 the date the reusable module 1401 was recharged and any other information related to the updated status of the reusable module 1401. Alternatively, the RFID tag 1402 may only contain identification information and the recharger 1410 can transmit the date the component was recharged and any other information to a central database (not shown). The reusable module 1401 can then be returned for use in the next dialysis session. It is understood that at least one multi-use module for any sorbent cartridge described in the present invention is described, such that two, three, four, or more multiuse modules, a non-limiting example being the multiuse module 1401, of various sizes, shapes, configurations, and function is contemplated. Additionally, at least one single-use module, a non-limiting example being the consumable module 1403, is contemplated such that two, three, four, or more single-use modules of various sizes, shapes, configurations, and function can be used in any sorbent cartridge of the invention.

Multi-Use Cartridge Protective System

In any embodiment of the first, second, third, or fourth aspects of the dialysis system, the authentication system can be a protective system to manage the safe use of a multi-use cartridge, or a cartridge having one or more reusable modules, during hemodialysis therapy. Multi-use cartridge protective systems can be designed to verify the volume of recharge solution used to recharge the single-patient, multi-use cartridge, monitor the conductivity of the incoming recharge solution is within the acceptable range, monitors the effluent temperature/time for the disinfection cycle of the single-patient, multi-use cartridge, monitors the water conductivity during rinse to verify recharge solution has been completely removed, and verifies a complete recharge cycle was performed prior to writing data to the RFID. The system also has been designed to protect patient safety by responding to possible misuse conditions.

Figure 15:
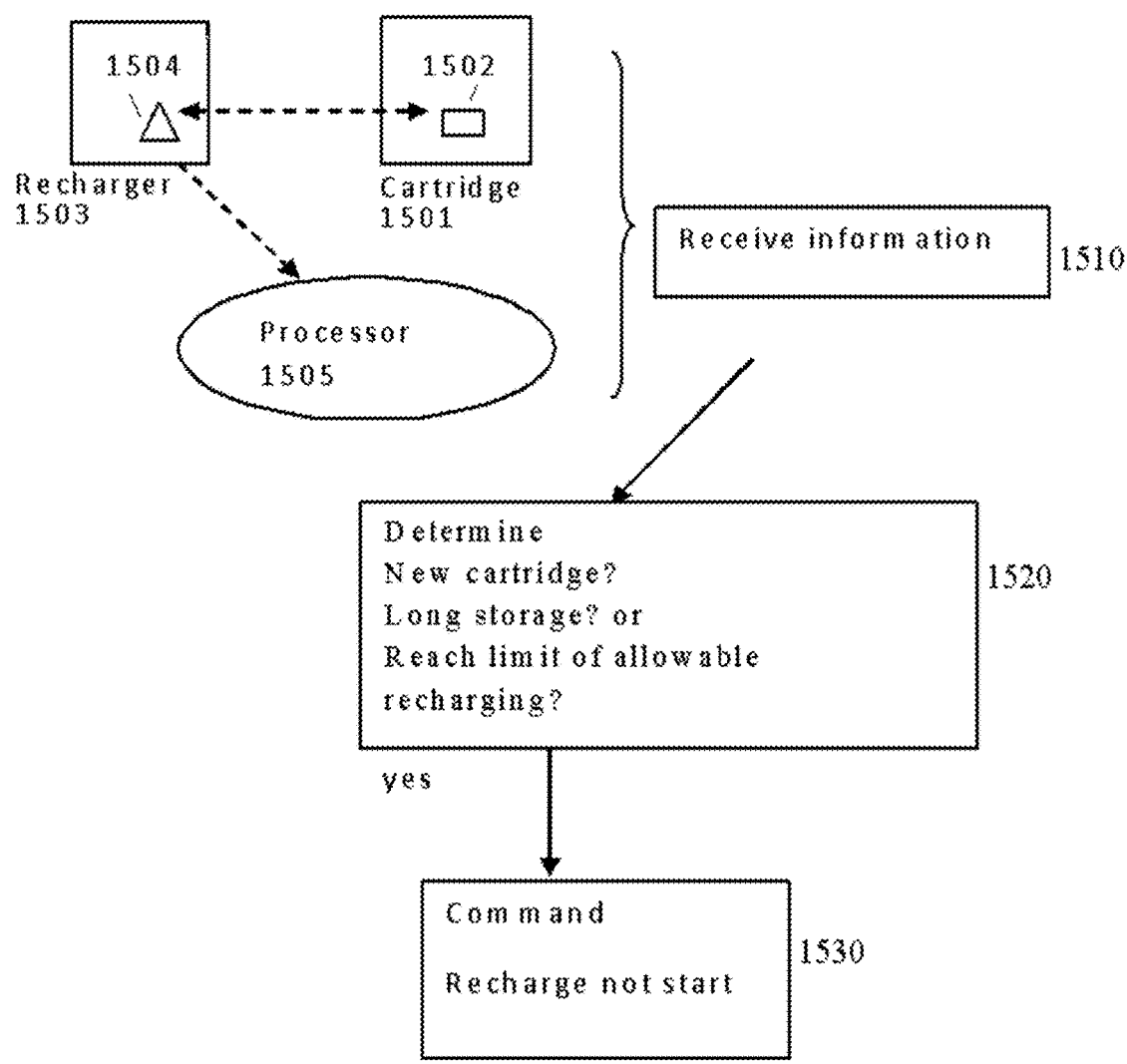
FIG. 15 shows diagrams of an authentication system managing safe recharging of a rechargeable cartridge.

Managing the use of the multi-use cartridge can include, but not limited to, the safe recharging of the multi-use cartridge of FIG. 15 and the safe application of the multi-use cartridge in the hemodialysis system (HDS) of FIG. 16.

FIG. 15 shows that a multi-use cartridge 1501, or a reusable module, contains an authentication component 1502, which stores information of the multiuse cartridge 1501. The authentication component 1501 can be read by a reader 1504 affixed on a recharger 1503, where the information can be transferred from the reader 1504 to a processor 1505. The processor 1505 receives the information at step 1510. The processor 1505 then makes determination at step 1520 regarding the multi-use cartridge 1501 based on the information received. For example, if the cartridge 1501 is found to be a new cartridge or a used cartridge that has been stored for a relatively too long time, the processor 1505 determines that the recharging process will not start, and subsequently controls the recharger 1503 not to start the recharging at step 1530. A person skilled in the art will understand that any further requirements for the safe use and recharging of the multi-use cartridge may be considered by the protective system.

Figure 16A:
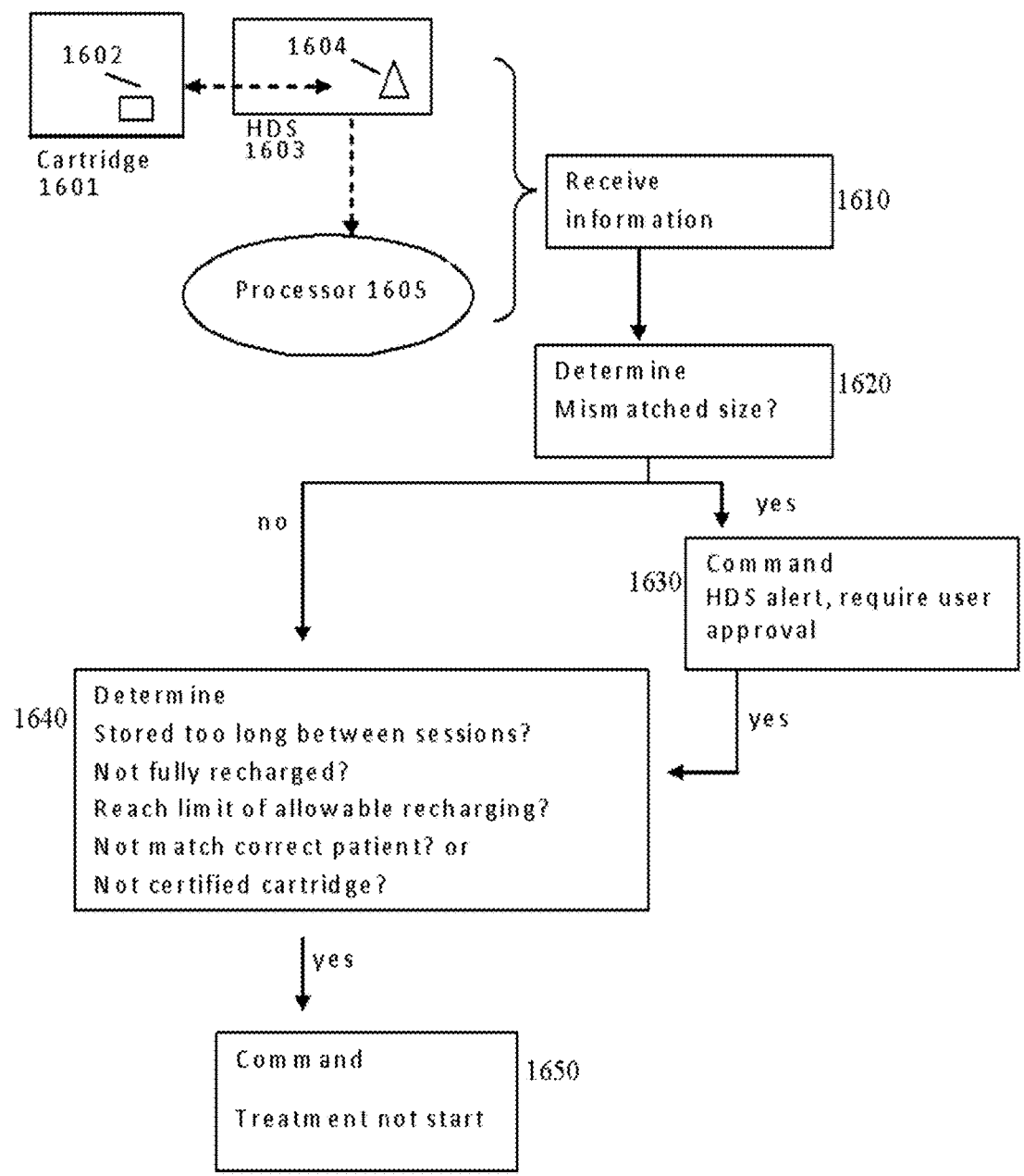
FIGS. 16a-16b show diagrams of an authentication system managing safe use of a rechargeable cartridge in dialysis.

FIG. 16a shows that a multi-use cartridge 1601 can contain an authentication component 1602, which stores information of the multi-use cartridge 1601. The authentication component, such as an RFID tag 1602, can be read by a reader 1604 affixed on an HDS 1603 at any suitable place, for example, a dialysis cabinet. Information contained in the RFID tag 1602 can be transferred from the reader 1604 to a processor 1605. The processor 1605 can receive the information of the RFID tag 1602 at step 1610, and make determination at step 1620. For example, the processor 1605 can determine whether the size of the cartridge 1601 matches the HDS and the patient. If the cartridge 1601 is found to be improperly sized, the processor 1605 generates an alert to the HDS at step 1607. The processor 1605 may also require the user to approve whether the mismatched cartridge 1601 can be used. If the user does not approve the use of the mismatched cartridge 1601, the processor 1605 can reject the use of the cartridge 1601. The user may replace the mismatched cartridge 1601 with a correct one and restart the authentication process or the user may choose to start the treatment (not shown). If the user approves the use of the mismatched cartridge 1601, the processor 1605 can determine other requirements for the proper use of the cartridge. Alternatively, the step 1640 can be omitted according to the user's discretion.

In non-limiting examples, the processor 1605 can also determine at step 1640 whether the cartridge 1601 has been stored for a relatively too long time between dialysis sessions, has been fully recharged, has reached limit of recharging, does not match the correct patient, or is not certified. If the answer is yes to any of these inquires, the processor 1605 can issue a command at step 1650 to disable the use of the cartridge 1601 and control the treatment not to start. A person skilled in the art will understand that any further requirements for the safe use and recharging of the multi-use cartridge may be considered by the protective system.

In non-limiting examples, the processor 1605 may be located within a console of the dialysis system. The console can implement an ultrafiltration controller and mechanisms that monitor and/or control the dialysate temperature, dialysate composition, the extracorporeal circuit, as well as blood and dialysate flow rates.

Figure 16B:
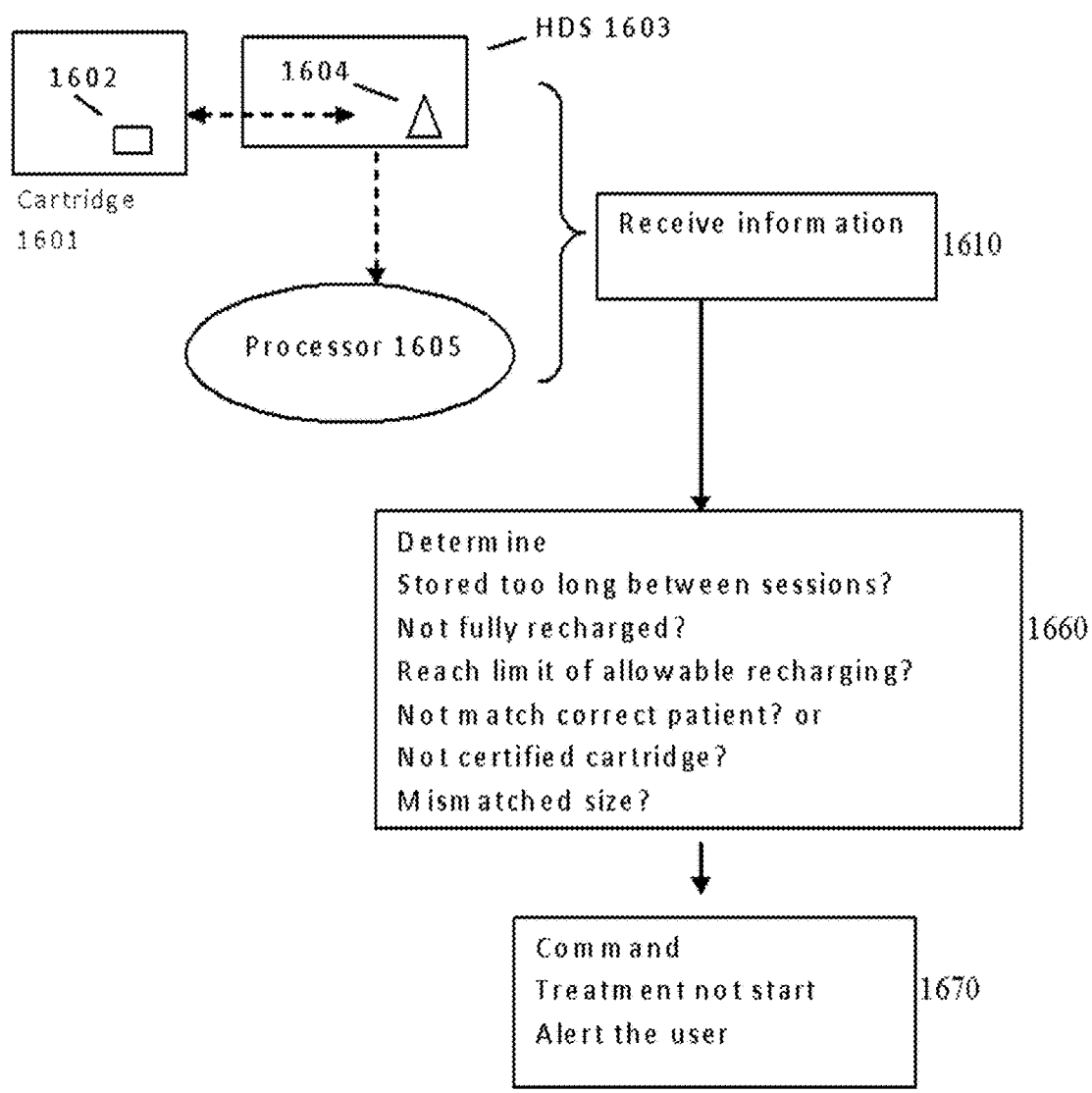

FIG. 16b shows non-limiting examples of the multi-use cartridge protective system. Same numerical references in FIG. 16a and FIG. 16b denote the same objects. In FIG. 16b, after the processor 1605 receives the information of the cartridge 1601 from the reader 1604 at step 1610, the processor 1605 determines at step 1660 whether the cartridge 1601 meets any of the following requirements: the cartridge 1601 has been stored too long between sessions, has not been fully recharged, has reached limit of allowable recharging, does not match the correct patient, is not a certified product, and has a mismatched size. If the answer is yes to any of these inquiries, the processor 1605 can disable the use of the cartridge 1601 and control the treatment not to start at step 1670. Additionally, the processor 1605 can display the particular reasons for the improper use of the cartridge 1601 on a user interface (not shown). For example, if the cartridge 1601 is found having a mismatched size, the processor 1605 may deliver a message to the user and require the user to replace the cartridge or approve the use of the mismatched cartridge 1601.

In non-limiting examples, the protective system of the multi-use cartridge 1601 may contain additional steps involving one or more of additional multi-use modules and single-use modules contained in the multi-use cartridge 1601. The protective system may also be related to consumable material contained in the multi-use cartridge 1601.

In any embodiment of the first, second, third, or fourth aspects of the invention, information used by a reprocessor or a recharger can be items including, but not limited to, when reprocessing program was last used, how many uses, use before date, cartridge size, regarding a reprocessing program. The reprocessing program may or may not need to meet a particular patient for therapy optimization. When the reprocessing or recharging program does not need to meet the particular patient, the patient information may not be necessary for the reprocessing program to proceed for therapy optimization.

Table 1 includes non-limiting examples of misuse of a recharging system based on information that can be contained in the authentication component and the determinations made by the system in response. Table 1 also includes exemplars of which types of misuse may be detected by particular components. One of skill in the art will understand that although Table 1 provides examples of components that can detect a particular misuse, any component in the system can be configured to detect a particular misuse, and in any embodiment, the authentication component can be read by a stand-alone identifier which can detect misuse. Further, Table 1 provides protective determinations made by the system in response to detecting misuse. One of skill in the art will understand that in any embodiment, any protective determination can be made, including alarms or notification to the user, and that the particular examples provided may be changed.

TABLE 1

Multiuse Cartridge RFID Safety Determinations

| Misuse | Detected By | Protective Determination |
|---|---|---|
| Recharge attempted on new cartridge | Recharger | Recharge process will not start |
| Used cartridge stored too long before starting recharge | Recharger | Recharge will not start - new multi-use cartridge needed |
| Recharged cartridge stored too long between sessions | Dialysis system | Treatment will not start - new recharge cycle required |
| Used cartridge not recharged or incomplete recharge cycle | Dialysis system | Treatment will not start until successful recharge |
| Multi-use cartridge reaches limit for number of recharges | Dialysis system and recharger | Treatment or recharging will not start |
| Recharged cartridge not matched to correct patient | Dialysis system | Treatment will not start |
| Mismatched single use and multi-use cartridge sizes | Dialysis system | System will alert user and require approval to start treatment |
| Cartridge are not manufactured by certified manufacturer | Dialysis system | Treatment will not begin |

Infusate Caddy Protective System

In any embodiment of the first, second, third, or fourth aspects of the invention, an infusate caddy protective system can determine whether the caddy is prepared for a specific patient and is installed appropriately in a dialysis system. Implementation of the infusate caddy protective system can include preparation of a caddy per the prescription of a particular patient and compare the patient information in the caddy with the patient information in a console, thus mitigating the risk of the caddy being installed and used on the wrong console/patient.

Figure 17A:
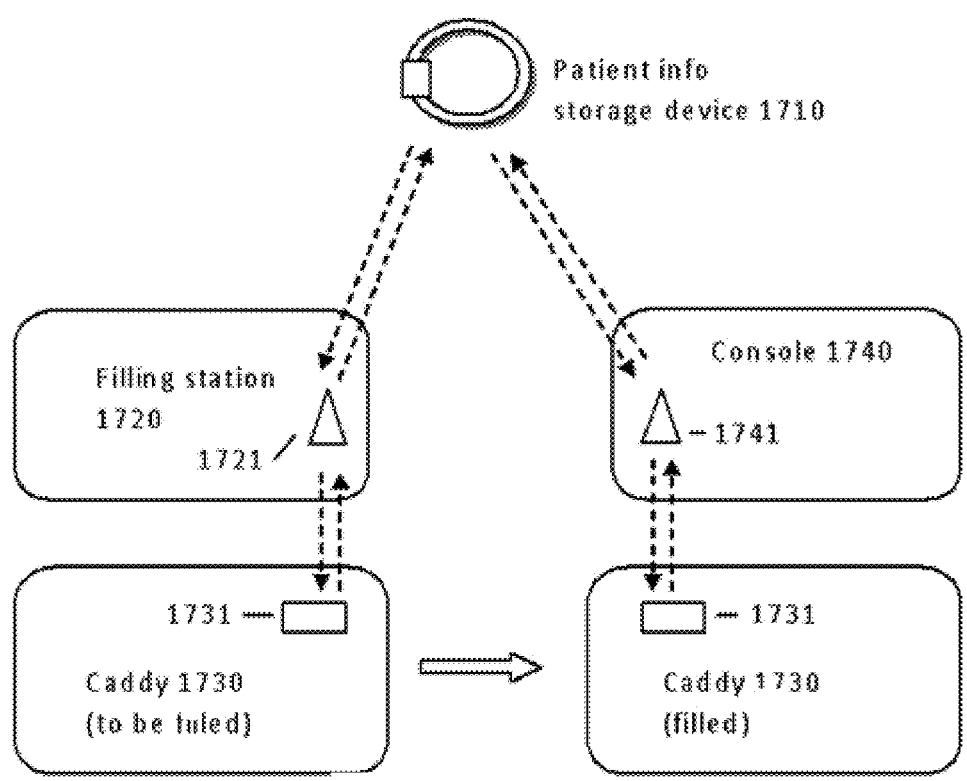
FIGS. 17a-17b show examples of an authentication system managing filling and safe use of a caddy in dialysis.

FIG. 17a shows an infusate caddy protective system containing a filling station 1720 having a reader 1721 to read a patient information storage device, such as a wrist-type RFID 1710. The filling station 1720 can also obtain the patient information from a different data source, such as a computer database having pre-stored patient information, or another authentication component attached to a dialysis component (not shown). After obtaining the patient information, the filling station 1720 can write the patient information onto an RFID tag 1731 of a caddy 1730. The caddy 1730 can be filled at the filling station 1720.

The RFID tag 1731 may contain additional information such as prior usage of the caddy 1730. The filling station 1720 can also determine whether the filling operation should be proceed based on the additional information of the caddy 1730, such as whether the caddy 1730 is a certified product, whether the prior usage of the caddy 1730 conflicts with the current filling (not shown).

In any embodiment of the first, second, third, or fourth aspects of the invention, the caddy 1730 can contain multiple containers each to be filled with different infusate solutions based on the prescription of a particular patient. The RFID tag 1731 may include, but not limited to, the patient prescription and the updated filling status of the caddy 1730.

The infusate caddy protective system can further include a console 1740 having a reader 1741 as shown in FIG. 17*a*. The reader 1741 can store patient information previously read from the patient information storage device 1710. The reader 1741 can also read the RFID tag 1731 of the caddy 1730, when the caddy 1730 is brought close to or installed in the console 1740. The reader 1741 can obtain the patient information and other information stored in the RFID tag 1731. The reader 1741 or a separate processor (not shown) of the console 1740 can then compare the information obtained from the caddy 1730 and the patient information read directly from the patient storage device 1710.

Figure 17B:
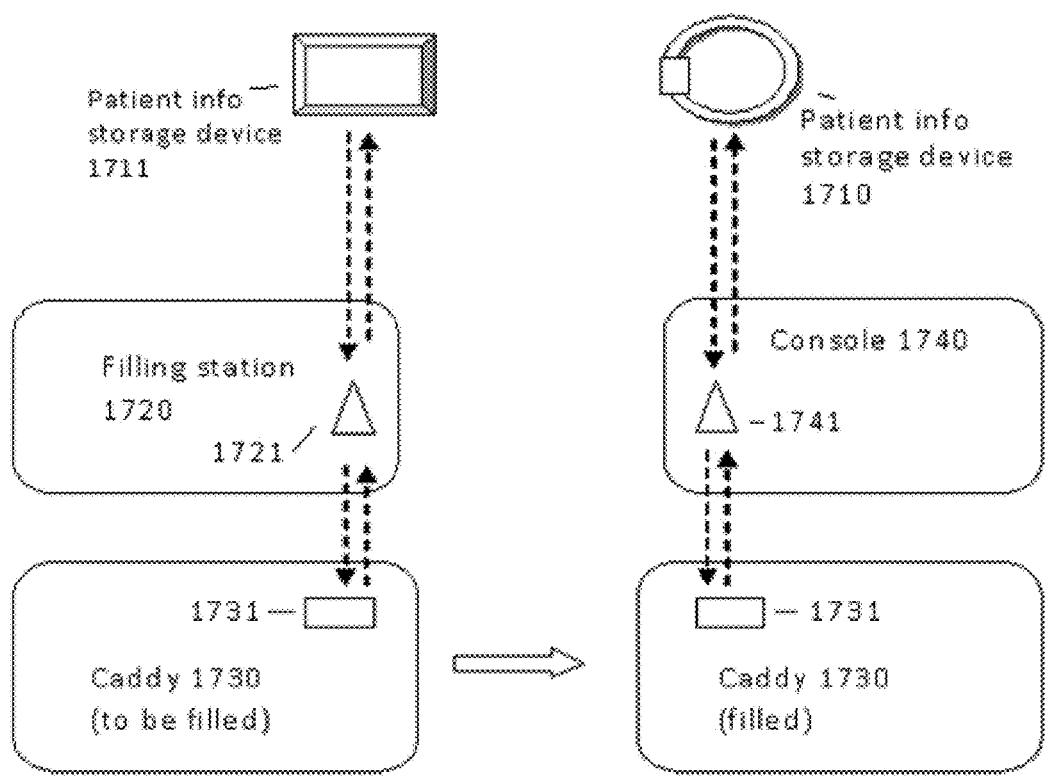

In a non-limiting example, as shown in FIG. 17*b*, the caddy 1730 can be positioned at a different location other than where the treatment would occur, and the filling station 1720 may read the patient information from a different data source 1711, which is different from the data source of the wrist-type RIFD 1710, which is read by the console 1740 where treatment is to occur. In other embodiments, any suitable position for the caddy 1730, filling station 1720, or console 1740 relative to each other for dialysis therapy, recharging, or convenience is contemplated. The console 1740 can determine whether the caddy 1730 is applied to the right patient and installed to the right console based on the information from different data sources, such as patient information storage devices 1711 and/or 1710. The console 1740 may also determine, for example, whether the caddy 1730 is a certified product and within a life of usage, which may not necessarily require the patient-specific information. It will be understood that additional combinations of patient storage devices can be matched to the filling station and console. For example, at least one patient information storage device 1711 and/or at least one patient information storage device 1710 can be affixed to any combination of dialysis components for identification. For example, two or more patient storage devices 1711 can be affixed to two or more modules for separate tracking and identification by either the console 1740 or filling station 1720, or both. Similarly, the wrist-band type patient info storage device 1710 can be used with either the console 1740 or filling station 1720, or both, as shown in FIG. 17*a*.

Figure 18:
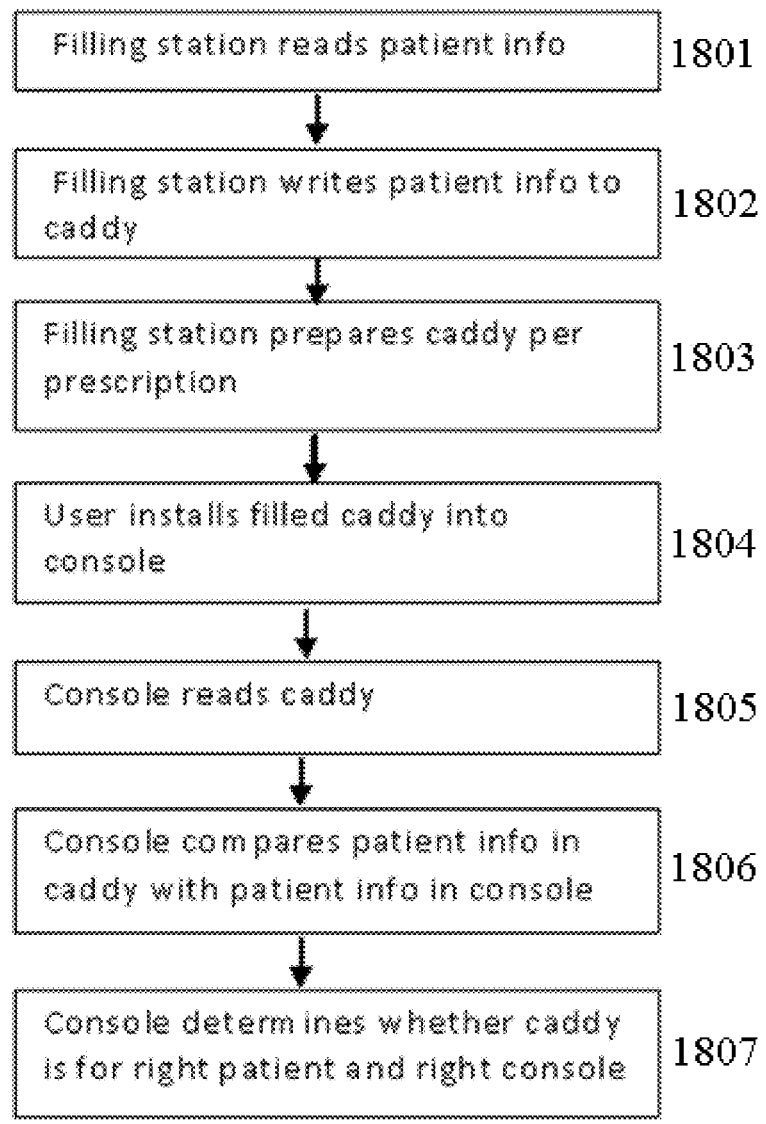
FIG. 18 shows diagrams of an authentication system managing filling and safe use of a caddy in dialysis.

FIG. 18 shows the operation of the infusate caddy protective system in FIG. 17*a* or *b*. At step 1801 of FIG. 18, the filling station can read patient information including the prescription through a reader attached on the filling station. The reader of the filling station can write the patient information onto an RFID tag of the caddy at step 1802. The caddy can be filled according to the prescription of the particular patient by the filling station at step 1803, where the filling status of the caddy may be updated onto the RFID of the caddy. At step 1804, the filled caddy can be installed into the console at step 1804. The console then can read the RFID tag on the caddy at step 1805 through a reader on the console, and compares the patient information obtained from the caddy and the patient information previously stored in the console at step 1806. The console can determine whether the caddy is provided for the right patient and installed to the right console at step 1807, based on the comparison result obtained at step 1806.

In non-limiting examples, if the console determines that the caddy is for the right patient and installed to the right console, the console can issue a command to proceed with the dialysis, or making determination with respect to other dialysis components (not shown). If the console determines that the caddy is not for the right patient or for the right console, the console can issue an alert to notify the user, and will not start the dialysis (not shown).

Sorbent Dialysis System

Figure 19:
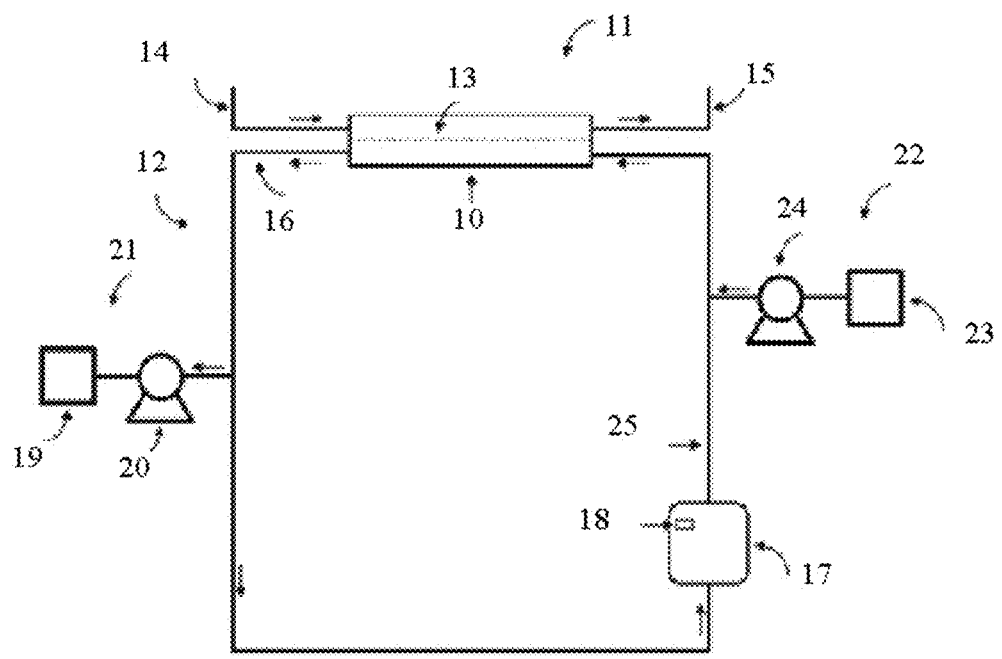
FIG. 19 shows a sorbent-based dialysis system having a blood circuit and a dialysis circuit.

FIG. 19 shows a sorbent dialysis system including a blood circuit or flow path 11, and a dialysate regeneration circuit or flow path 12, separated by a membrane 13 of the dialyzer 10. The blood enters the dialyzer 10 through a blood line inlet 14 and exits through a blood line outlet 15. The dialysate flow loop 12 is a controlled compliant flow loop. The blood flowing through the dialyzer 10 via flow path 11 can exchange waste compounds across the membrane 133 with the dialysate flowing through the dialyzer 10 via flow path 12.

The dialysate that has gone through the dialyzer 10 exits as spent dialysate 16. The spent dialysate may pass an ultrafiltration system 21, which can include an ultrafiltration pump 20 and ultrafiltration reservoir 19. The ultrafiltration pump 20 can remove fluid from the dialysate flow path 22, which draws fluid across the membrane 13 from the blood. The fluid removed by the ultrafiltrate pump 20 is collected in ultrafiltrate reservoir 19.

Regeneration of dialysate in the dialysate regeneration flow path 12 occurs at the reusable sorbent cartridge 17. The sorbent cartridge 17 contains sorbent materials that can remove specific toxins from the dialysate, or break down toxins into non-toxic compounds. After exiting the sorbent cartridge 17, the clean dialysate may lack certain ions, such as potassium, calcium, or magnesium, which need to be added before re-entering the dialyzer 10. This can be accomplished by the infusate system 22. The infusate system 22 can comprise infusate pump 24 and infusate reservoir 23. The infusate reservoir 23 may contain a concentrated solution containing the specific ions that need to be added to the dialysate before crossing into the dialyzer 10. After passing through the infusate system 22, the dialysate is fully regenerated and can pass back through the dialyzer 20.

The sorbent cartridge 17 may be reusable. In order to ensure that the cartridge 17 is a certified component, correctly matched to the correct machines, and still within the cartridge's useful life, an identification component 18 may be attached to the cartridge 17, or embedded within the cartridge 17.

When dialysis is complete, the reusable sorbent cartridge 17 may be removed from the dialysis circuit 12. This can be performed to replace the cartridge 17, or to recharge the sorbent materials within the cartridge 17. After the sorbent cartridge 17 is placed back into the circuit 12 of FIG. 19, a reader (not shown) can read the identification component 18 to make sure that the correct cartridge is being used. The identification component or authentication component may additionally, or alternatively, be affixed to any of the components of the dialysis system described.

The first, second, third, and fourth aspects of the present invention provide an authentication system to manage the dialysis system for the purposes of achieving therapy optimization. The authentication system manages the proper use of certified products, and ensuring patient's safety and system efficiency, in addition to protecting the manufacture's economic interests against counterfeit products.

The authentication system also improves the proper use of the certified products through monitoring the recharging operation, use of consumables, and other settings of the dialysis system in order for optimized setting of the dialysis system. The authentication system also provides a patient information storage device for the storage, access, and update of the patient's information through possibly remote and automatic processes. The authentication system can associate the patient's information with one or more particular dialysis components and determine whether optimized setting is available for the dialysis system.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In any embodiment of the first through seventh aspects of the invention, an article of manufacture may comprise one or more computer system-readable storage media.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A dialysis authentication system, comprising:
   a sorbent cartridge containing one or more sorbent materials, and a recharger for recharging one or more sorbent materials in the sorbent cartridge;
   at least one authentication component for managing a sorbent-based dialysis system containing data corresponding to at least one of the sorbent cartridge or recharger;
   at least one identifier to read the data of the at least one authentication component; and
   a processor to receive the data from the at least one identifier, wherein the data are processed by the processor for making a determination regarding the at least one of the sorbent cartridge or recharger;
   wherein the data from the authentication component and a patient authentication component are communicated to the processor; wherein the processor executes instructions for determining an optimized setting of the dialysis system for a patient regarding the sorbent cartridge or recharger; wherein the optimized setting of the dialysis system comprises whether any one of the sorbent cartridge is fully recharged, whether the sorbent cartridge matches the dialysis system, whether settings of the dialysis system are proper for the patient, whether the sorbent cartridge matches a patient prescription, a blood flow rate, sorbent cartridge size, ultrafiltration rate, ultrafiltration profile, and combinations thereof.

2. The dialysis authentication system in claim 1, wherein the authentication component is affixed on any one or more selected from the group of a dialyzer, sorbent cartridge, and recharger.

3. The dialysis authentication system of claim 1, wherein the authentication component is selected from a group comprising a radio-frequency identification (RFID) marker, a bar code, a one-wire security component, and a wireless authentication component.

4. The dialysis authentication system of claim 1 wherein the authentication component contains an embedded memory.

5. The dialysis authentication system of claim 1, wherein the authentication component contains a radio-frequency identification (RFID) chip and a Memory chip bonded in a smart card.

6. The dialysis authentication system of claim 1, wherein the authentication component is readable and writable that allows the data of the sorbent cartridge or recharger to be updated.

7. The dialysis authentication system of claim 1, wherein the processor determines non-certified components or counterfeit components based on the data received from the authentication component.

8. The dialysis authentication system in claim 1, wherein the patient authentication component is one of an implantable device, a card-like device, and a wrist-band device.

9. The dialysis authentication system of claim 1, wherein the processor determines one or more of whether the sorbent cartridge or recharger matches the patient, whether a setting of the sorbent cartridge or recharger is proper, and any changes of the setting to be made for optimized performance, based on the data received from the authentication component and the patient authentication component.

10. The dialysis authentication system in claim 1, wherein the identifier is affixed onto a second dialysis component to read the authentication component, and the processor determines whether the dialysis component having the authentication component matches the second dialysis component.

11. The dialysis authentication system of claim 1, wherein the identifier is a multimode type reader that is able to communicate with at least two different types of the authentication component.

12. The dialysis authentication system of claim 1, wherein the at least one authentication component includes two or more authentication components, and the identifier distinguishes the two or more authentication components from each other.

13. A method of managing a dialysis system for performing dialysis via radios signals, comprising:
   providing the dialysis authentication system of claim 1;
   reading a first data from a first authentication component corresponding to a first dialysis component by the at least one identifier;

reading a second data from a second authentication component corresponding to a second dialysis component or the patient by the at least one identifier;
receiving the first data and the second data by the processor from the at least one identifier;
making a determination by the processor based on the first data and the second data regarding the first dialysis component in view of the second dialysis component or the patient; and
controlling a setting of the first dialysis component for optimized performance in view of the second dialysis component or the patient.

14. The method of claim 13, further comprising storing data in at least one of the first authentication component and the second authentication component regarding the dialysis, during or after the dialysis ends.

15. A method comprising the steps of:
providing the dialysis authentication system of claim 1;
reading data from the at least one authentication component affixed on a rechargeable component used in sorbent based dialysis by the at least one identifier;
communicating the data derived from the at least one authentication component to the processor;
determining whether to start a recharge of the rechargeable component by the recharger based on the data received by the processor; and
controlling the recharger used to recharge the rechargeable component to selectively recharge based on the determination made by the processor.

16. The method of claim 15, wherein the step of determining further comprises the step of determining one or more of whether the rechargeable component is stored too long using a predetermined standard, whether the rechargeable component is not fully recharged, and whether the rechargeable component reaches a limit of recharging.

17. A method comprising:
providing the dialysis authentication system of claim 1;
reading data of an authentication component affixed on a multi-use cartridge by an identifier affixed on a hemodialysis system;
communicating the data of the authentication component to the processor by the identifier;
determining by the processor whether the cartridge is to be properly used according to the data communicated to the processor; and
controlling a hemodialysis therapy according to the determination made by the processor.

18. The method of claim 17, wherein the step of determining comprises determining one or more of whether the cartridge is stored too long according to a predetermined standard, whether the cartridge is not fully recharged, whether the cartridge reaches a limit of recharging, and whether the cartridge matches a patient.

19. The dialysis authentication system of claim 1, wherein the patient authentication component stores whether ammonia breakthrough occurred in at least one prior session.

20. The dialysis authentication system of claim 19, wherein if ammonia breakthrough occurred in the at least one prior session, the processor determines that the optimized setting includes a larger sorbent cartridge size.

* * * * *